United States Patent [19]

Langerman

[11] Patent Number: 5,628,795

[45] Date of Patent: May 13, 1997

[54] SPARE PARTS FOR USE IN OPHTHALMIC SURGICAL PROCEDURES

[76] Inventor: David W. Langerman, 99 Dutch Hill Plz., Orangeburg, N.Y. 10962

[21] Appl. No.: 405,255

[22] Filed: Mar. 15, 1995

[51] Int. Cl.$^6$ .................................. A61F 2/14; A61F 2/16
[52] U.S. Cl. ......................... 623/6; 623/4; 623/5; 623/66
[58] Field of Search ........................... 623/4–6, 66

[56] References Cited

U.S. PATENT DOCUMENTS

| | | | |
|---|---|---|---|
| 4,888,016 | 12/1989 | Langerman | 623/6 |
| 4,946,469 | 8/1990 | Sarfarazi | 623/6 |
| 4,963,148 | 10/1990 | Sulc et al. | 623/6 |
| 5,026,396 | 6/1991 | Darin | 623/6 |
| 5,092,880 | 3/1992 | Ohmi | 623/6 |
| 5,275,623 | 1/1994 | Sarfarazi | 623/6 |
| 5,275,624 | 1/1994 | Hara et al. | 623/6 |

FOREIGN PATENT DOCUMENTS

| | | | |
|---|---|---|---|
| 9305733 | 4/1993 | WIPO | 623/6 |

*Primary Examiner*—Mary Beth Jones

*Attorney, Agent, or Firm*—Norbert P. Holler

[57] ABSTRACT

Ophthalmic "spare parts" which are made of biocompatible material and may be implanted by a surgeon in either the ciliary sulcus or the residual natural capsular bag of a patient's eye following cataract surgery so as to serve as a receptacle for an IOL or other optical or mechanical device, may have the form of an either anteriorly incomplete and posteriorly complete capsular bag-like structure with a generally toroidal equatorial region, or the form of a both anteriorly and posteriorly incomplete generally toroidally ring-shaped capsular bag-like structure, the interior space of the toroidal part of the structure between the anterior and posterior walls constituting a compartment, which may be divided into two subcompartments by an interior circumferential rib, into which an optical or other device may be inserted. The capsular bag-like structures can also serve to provide an enhanced capability of inhibiting posterior capsular opacification in the residual natural capsular bag, can have a circumferentially resiliently compressible split washer-like configuration, and can have visually perceptible features on the anterior and/or posterior walls to facilitate manipulation and/or orientation of those structures and the optical or other devices being inserted therein.

49 Claims, 11 Drawing Sheets

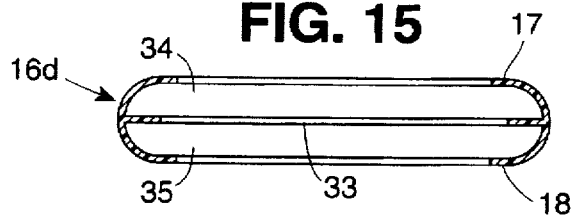
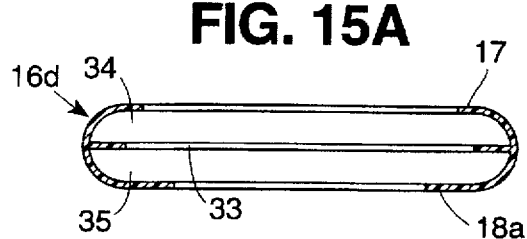
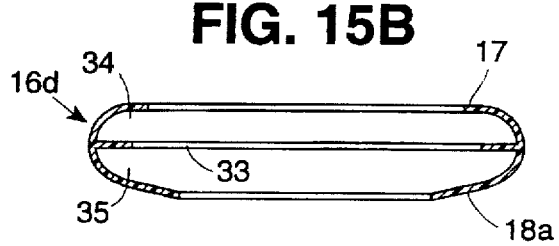
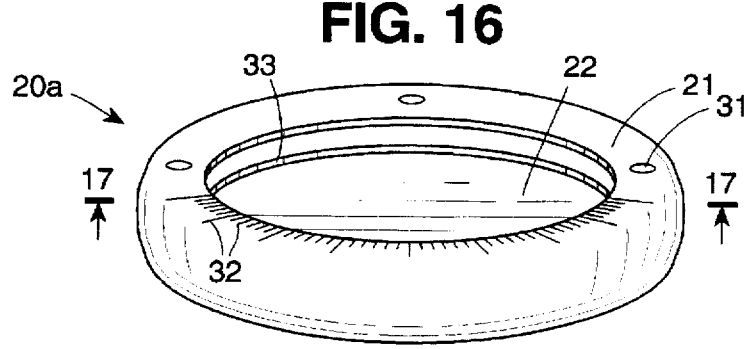
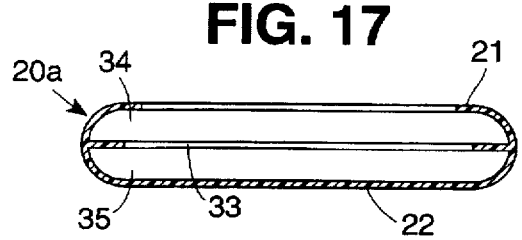
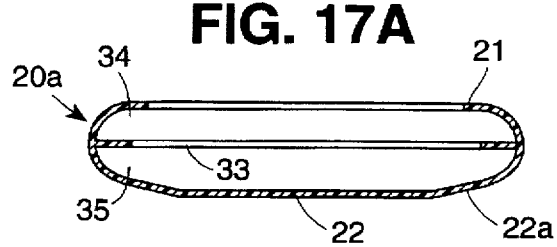

SPARE PARTS FOR USE IN OPHTHALMIC SURGICAL PROCEDURES

This invention relates to the art of ophthalmic surgical procedures, and in particular to a class of novel "spare parts" which are adapted for use by ophthalmic surgeons in the course of those surgical procedures which involve the removal of a cataract from a human eye.

BACKGROUND OF THE INVENTION

Generally speaking, the portion and components of a human eye with which the present invention is most closely concerned, though well known to those skilled in the art, are illustrated and labeled for lexicographic purposes in FIG. 1 of the hereto appended drawings. The eyeball (which is suspended in the orbit by various types of tissues and muscles and is protected in front by the upper and lower eyelids, all not shown) is enclosed in three layers or coats of which only the outer one, the sclera, is explicitly represented (the other layers being the retina and the choroid coat). At the front of the eye, the place of the sclera, which is white and opaque, is taken by the cornea, which is transparent and adjoins the sclera at the limbus under the conjunctiva. The posterior part of the eyeball is enclosed by Tenon's capsule which is connective tissue that extends anteriorly to the conjunctival fornix and is continuous with the muscular fascia of the eye. Interiorly of the eyeball and located behind the cornea are the iris and the lens, with the lens being suspended in place by the ciliary zonule or zonular fibers which are connected at one end to the lens and at the other end to the ciliary body. The iris, which normally rests against the front of the lens (although for the sake of clarity it is shown in FIG. 1 as being spaced somewhat therefrom) is actually a continuation of the choroid coat starting from a location just anteriorly of the ciliary body and is provided in the middle with a circular opening, the pupil, through which light entering the eye through the cornea is able to reach the lens. The space between the cornea and the iris constitutes the anterior chamber of the eye, with the peripheral channel or groove where the cornea and the iris meet in the limbal region of the eye constituting the angle of the anterior chamber. The space between the iris and the lens constitutes the posterior chamber. These two chambers, which communicate through the pupil, are filled with a watery fluid, the aqueous humor. The space in the eyeball behind the lens is filled with a transparent jelly-like substance, the vitreous humor. The lens itself includes a viscous nucleus of inert material enclosed by layers of fibers which in turn are surrounded by an elastic membrane or capsular bag. That part of the capsular bag which is located at the side of the lens facing toward the iris and the cornea is designated the anterior capsule, and that part of the capsular bag which is located at the side of the lens facing toward the retina and engaging the hyaloid face of the vitreous humor is designated the posterior capsule. The hyaloid face is a skin-like somewhat denser region of the vitreous humor which constitutes the boundary of the latter at its interface with the posterior capsule and the ciliary zonule. The cornea, the aqueous humor, the lens and the vitreous humor constitute the refractive media through which light entering the eye passes prior to reaching the retina, with the cornea constituting the main light-refracting structure while the lens, a relatively minor part of the overall optical system, constitutes principally the means of varying the focus.

As is well known, human beings, especially elderly persons, tend to develop a degree of opacity or clouding of the lens fibers surrounding the inert nucleus. The condition where this opacity spreads into the center of the lens in the region behind the pupil so as to impair vision, is designated cataract. When the opacity has progressed sufficiently to cause the loss of useful functional vision, the cataract is said to be mature, and the only currently available treatment for that condition is the removal of the cataract by extraction of the lens from the eye. Such a cataract removal, which is a very delicate operation but probably one of the most common and widely performed ophthalmic surgical procedures these days, may involve either an intracapsular or an extracapsular extraction of the lens.

In an intracapsular cataract extraction (ICCE), the entire lens, including the nucleus, the cortex (the fibers) and the enveloping capsular bag, is taken out as a unit, with the zonular fibers which connect the bag to the ciliary body being first dissolved and the cataract then being removed with the aid of a low temperature probe. In such a case, it was initially the practice, in the early stages of the development of artificial lenses, to follow up the removal procedure by the implantation of an intraocular lens (IOL) into the anterior chamber of the eye, with the lateral position fixation elements or haptics (resilient loops, arms, or the like) of the IOL being received in the angle of the anterior chamber. However, as the structural and functional characteristics of intraocular lenses were modified and improved over the years and as the surgical techniques and skills for the successful implantation of such lenses have become more refined and sophisticated, it became acceptable, as a follow-up to an ICCE, to implant the IOL in the posterior chamber, with the haptics or position fixation elements being received in the ciliary sulcus (which is the juncture region between the iris and the ciliary body and is generally shallow or flat but, merely for the sake of clarity, has been illustrated in FIG. 1 in a somewhat exaggerated fashion as having the form of a relatively deep channel or groove), subject to the provision that steps are taken to ensure that the IOL does not fall into the vitreous humor.

In an extracapsular cataract extraction (ECCE), by way of contrast, first a major portion of the anterior capsule is cut away, leaving in place only that part of the natural or endogenous capsular bag which consists of the posterior capsule and the remaining, generally annular, anterior capsular flap. Then the lens nucleus is extracted from the capsular bag by any well-known type of expression or by phacoemulsification, and finally the cortex is removed by irrigation and aspiration. In such a case, the current practice is to follow up the removal procedure by the implantation of an IOL into the posterior chamber of the eye, with the haptics or position fixation elements being received either in the ciliary sulcus, where the residual portion of the endogenous capsular bag constitutes the means for preventing the IOL from falling into the vitreous humor, or in the residual capsular bag itself at the equatorial region thereof, i.e., where the anterior capsular flap adjoins the posterior capsule.

Irrespective of whether the procedure performed is an ICCE or an ECCE, sooner or later the surgeon may be faced with the post-operative necessity of having to implant any of a number of optical or mechanical devices into the patient's eye. The desired implant may, as stated above, be an optical device such as an IOL (which may be a multi-focal lens, or a lens specifically designed for monocular vision, toric vision, low vision, etc., or even a single-lens or multiple-lens system designed to provide an appropriate degree of correction for astigmatism or macular degeneration), or a mechanical device such as a semipermeable membrane to keep the vitreous humor or other fluids from migrating from the posterior chamber into the anterior chamber while permitting passage of such substances as nutrients, electrolytes, aqueous humor, etc., or a partly mechanical, partly optical device such as a pseudo iris to replace a natural iris which has been surgically removed because of mechanical damage, attack by a cancer, etc. While surgical procedures for effecting such implantations have become quite well known and common over the years and generally pose no difficulties to an experienced ophthalmic surgeon, some patients have nevertheless developed more or less severe post-implantation trauma or after-effects in the form of loss of visual acuity or physical pain or both, which may be due to any of a number of different causes, such as, for example, posterior capsular opacification (resulting from migration of residual epithelial cells from the equatorial region of the capsular bag onto and over the posterior capsule to the medial region thereof intersecting the optical axis of the patient's eye), decentration of the IOL (resulting from a lateral shifting of the IOL out of its desired optimum position either during or after the implantation thereof), etc.

In U.S. Pat. No. 4,888,016, there are disclosed a number of "spare parts," having a variety of structures and shapes, which are designed for implantation into an eye as an adjunct to cataract surgery, principally to facilitate the repair and/or reinforcement and/or replacement of damaged or diseased eye components. Basically, such "spare parts" are artificial members made of cohesive sheet materials of biocompatible substances such as cross-linked hyaluronic acid (including the sodium, potassium and other salts of the acid), polymethyl methacrylic acid (PMMA), silicone, hydrogel or other equivalent substances. One of the types of "spare parts" disclosed in the said patent is a sheet member which has been preformed into the shape and configuration of an artificial capsular bag-like structure that either is an anteriorly incomplete but posteriorly complete capsular bag, i.e., it is a capsular bag-shaped structure having a full posterior capsule portion and an annular anterior capsular flap-like portion connected along its outer periphery to the outer periphery of the posterior capsule portion (i.e., equatorially of the bag), or is a both anteriorly and posteriorly incomplete capsular bag, i.e., a generally toroidal ring-shaped structure having an annular posterior capsular flap-like portion and an annular anterior capsular flap-like portion and thus being essentially similar in form to the original endogenous capsular bag with the central regions of the anterior and posterior capsules both cut away. That type of "spare part" is described in the '016 patent as being designed for surgical implantation either into the residual endogenous capsular bag which remains in the patient's eye after an extracapsular cataract extraction (in this case the exterior peripheral regions of the anterior and posterior capsule portions of the "spare part" are smooth-surfaced) or into the region of the eye which is surrounded by the ciliary body and from which the entire original endogenous capsular bag has been removed by an intracapsular cataract extraction (in this case the "spare part" is provided along the exterior peripheral surface regions of its anterior and posterior capsule portions with a plurality of circumferentially distributed, generally radially extending artificial zonular fibers, also made of the hyaluronic acid or comparable sheet material, to enable the "spare part" to be connected to and supported by the ciliary body).

In U.S. Pat. No. 5,366,501, there is disclosed a "spare part" in the form of an IOL which is specially designed to help prevent the post-operative occurrence of posterior capsular opacification following an ECCE. To this end, the IOL is provided with a dual 360° haptic structure in the form of a pair of concentric rings encircling the central optic or lens body. Of these haptics, the inner ring is spaced from and secured to the outer periphery of the optic by an opposed pair of diametrically aligned generally rod-shaped first bridging elements, while the outer ring is spaced from and secured to the outer periphery of the inner ring by an opposed pair of diametrically aligned generally rod-shaped second bridging elements which are aligned with the first bridging elements and are so oriented as to dispose the inner haptic posteriorly offset somewhat relative to the outer haptic. By virtue of this construction, when such an IOL is implanted in the residual capsular bag of the eye, the outer haptic (which is seated in the equatorial region of the capsular bag) serves as a primary barrier against migration of epithelial cells from the equatorial region of the bag onto the posterior capsule, and the inner haptic (which bears against the anterior surface of the posterior capsule at a location between the equatorial region and the mid-region of the posterior capsule) serves as a secondary barrier for blocking migration into the mid-region of the posterior capsule of any epithelial cells that were not blocked by the outer haptic. At the same time, the offset between the inner and outer haptics also ensures that the optic is pressed against the posterior capsule so as to inhibit the formation of Elschnig's pearls on the posterior capsule.

BRIEF DESCRIPTION OF THE INVENTION

It is an object of the present invention to provide an ophthalmic surgeon with a class of new and improved circumferentially generally ring-shaped "spare parts" which are made of the biocompatible materials disclosed in the aforesaid U.S. Pat. No. 4,888,016 and are designed and constructed for implantation, either alone or in conjunction with one or more optical and/or mechanical and/or combined optical and mechanical devices, into the patient's eye after the performance of either an intracapsular or an extracapsular cataract extraction.

It is another object of the present invention to provide such novel and improved "spare parts" which are formed and designed either for implantation into the residual endogenous capsular bag of the eye following an ECCE or for implantation into the region of the ciliary or scleral sulcus of the eye and which may, when so implanted, serve as a receptacle or other type of support for an implanted device as aforesaid while also affording improved resistance to decentration of the implanted device.

It is yet another object of the present invention to provide such "spare parts" which, whether intended for implantation in the ciliary or scleral sulcus or in the residual capsular bag, have the form of either an anteriorly incomplete but posteriorly complete capsular bag-like structure or a both anteriorly and posteriorly incomplete generally toroidally ring-shaped structure.

It is still another object of the present invention to provide such structures which are equipped with means visually perceptible by the surgeon, and if need be also physically engageable by the surgeon with the aid of a tool, during the implantation phase of the operation for facilitating rotational adjustments of the disposition, in the eye, of either such a structure or an associated optical or mechanical device while the same is being inserted into the eye.

More particularly, it is contemplated by the present invention that those artificial "spare parts" which are herein disclosed and are designed for insertion into the patient's endogenous residual capsular bag, irrespective of whether the latter is damaged or not, will serve in the first instance as a carrier or receptacle for an IOL, irrespective of whether the IOL is a single- or multiple-lens system. To this end, the outer equatorial diameter of the inserted "spare part," irrespective of whether such a "spare part" is shaped like an anteriorly incomplete capsular bag or like a both anteriorly and posteriorly incomplete capsular bag-derived toroidal ring, preferably should be about 10.5 mm but in any event somewhat, on the order of between about 0.5 mm and 1.5 mm, greater than the inner equatorial diameter of the residual capsular bag. By virtue of this size differential, the implanted "spare part" will serve to expand and strengthen the residual capsular bag in the event some of the ciliary zonules are weakened or torn, or in the event the bag itself is weakened by a tear in the posterior capsule or in the anterior capsular flap or by a tear which extends from the anterior capsular flap into the posterior capsule. Any of these conditions, of course, could create instability for the IOL, and such instability, it will be understood, could result in decentration of the IOL (decentration, which is to be avoided in any event, would be especially harmful in the case of an implanted multi-focal lens).

Within this context, such a toroidal ring-like structure or such an anteriorly incomplete capsular bag-like structure may be provided on the outer surface of its anterior wall or capsular flap-like portion with visually perceptible degree markings or indicia in the form of a series of uniformly spaced radial lines at suitable spacings from each other. Such degree markings would preferably be provided only along one half (the upper half as viewed by the surgeon during the operation) of the full circumference of the anterior wall or capsular flap-like portion of each ring or bag-like structure, so that the 0° mark in each eye will be located at the 3 o'clock position, the 90° mark at the 12 o'clock position, and the 180° mark at the 9 o'clock position, but the markings could, if desired, be provided around the full 360° circumference of the anterior wall, running from 0 to 180 in both directions. The precise magnitude of the intervals between adjacent degree marks is not critical, but it is currently preferred that the lines will be arranged at 5° spacings from each other. However, the intervals between the lines may actually be smaller than 5°, e.g., 3° or 4°, or larger than 5°, e.g., 6°, 9°, 10° or 15° or even as large as 20°, subject only to the overriding requirement that the resolution must be such as to leave the individual lines clearly visible to the surgeon. It will be understood, therefore, that with the aid of such a "spare part" the ability of the surgeon to implant a cylinder lens with the proper axis orientation for astigmatism correction will be greatly enhanced.

The same type of "spare part," furthermore, whether with or without any degree markings as aforesaid, may be provided with a plurality of visually perceptible indentations or holes, preferably two or three at 90° spacings, in either its lower or posterior wall or in its upper or anterior wall, which the surgeon can engage with a tool for effecting the proper positioning of the "spare part" in the residual capsular bag. This would actually be especially advantageous with a bag-like or ring-like structure having degree markings thereon.

Likewise independently of the presence or absence of any of the aforesaid features, the "spare part" may be provided with an internal equatorial rib or partition which effectively divides the space within the ring- or bag-like structure into two coextensive compartments (the rib may be continuous over the whole circumference or have a limited gap therein as long as its divider function remains unimpaired) adapted to receive and support separate single or multiple lenses or lens elements. Such a structure would be well suited to serve as a carrier for, by way of example, a sphere lens and a cylinder lens used for astigmatism correction, or for the components of a compound lens system used for correcting for macular degeneration. It should, however, be noted, in this regard, that the mentioned equatorial rib can be dispensed with in a "spare part," even though the same is intended to be used in correcting for macular degeneration, if the requisite compound lens system is relatively large or heavy by virtue of being composed of different lenses which may or may not be fused to one another.

The "spare parts" of the present invention which are intended for implantation into the residual natural capsular bag will also serve as aids against the occurrence and spread of posterior capsular opacification. Here the artificial anteriorly incomplete but posteriorly complete bagshaped insert or the both anteriorly and posteriorly incomplete ring-shaped insert will perform this function by virtue of the fact that the exterior surface of the posterior capsule portion or of the posterior capsular flap-like portion of the insert will closely engage the underlying portion of the anterior surface of the natural posterior capsule and thereby will impede migration of epithelial cells from the equatorial region of the capsular bag onto and over the posterior capsule. The cell migration-inhibiting effect will actually be best achieved by a construction of the insert in which the posterior capsular flap-like portion of the ring-shaped member or the corresponding region of the posterior capsule portion of the bag-shaped member is formed so as to be posteriorly inclined at an angle of about 10°–15° relative to the equatorial plane of the insert. This will enhance the pressure exerted by the insert against the natural posterior capsule and thereby will increase the likelihood that no epithelial cells will get past the surface contact region between the insert and the posterior capsule of the natural capsular bag.

It is also contemplated by the present invention that those artificial "spare parts" which are herein disclosed as being designed for placement into the eye in the region of the ciliary sulcus so as to serve as a support or carrier or receptacle for an IOL or other optical or mechanical device, will be used primarily when there is no whole posterior capsule present in the patient's eye, so that prevention of posterior capsular opacification is not a consideration. Thus, the implantation of such "spare parts" in the scleral region, i.e., in the region of the ciliary sulcus, of the eye will usually be decided upon by the surgeon either in a case where the operation was an ICCE, so that nothing of the original capsular bag has remained in the patient's eye, or in a case where, though the operation was an ECCE, for some reason the posterior capsule was damaged or removed with the lens nucleus during the cataract extraction and only the peripheral portion of the capsular bag consisting of the anterior and posterior capsular flaps remained as a residue of the bag in the eye. It should be noted, however, that a scleral ciliary sulcus mounting of such a "spare part" may be utilized even if the entire residual capsular bag (including the full posterior capsule and the anterior capsular flap) remains in the patient's eye, although in that case it may be advisable to provide some auxiliary means for inhibiting posterior capsular opacification of the bag.

It will be understood, therefore, that in the case of an ICCE the implanted artificial ring- or bag-like structure (this structure, like one which is designed for implantation into the residual natural capsular bag following an ECCE, will preferably have an outer diameter of about 10.5 mm) must be securely anchored to the sclera in the region thereof surrounding the ciliary sulcus in order to prevent the implanted structure and ultimately the IOL or other device supported thereby from falling into the vitreous humor. Such fixation can best be effected through the intermediary of a plurality of spines affixed to the outer periphery of the ring- or bag-like structure, with the spines extending generally radially outwardly from the structure at equiangular spacings. The spines, which must be capable of penetrating into or perforating (i.e., penetrating entirely through) the sclera in the region thereof surrounding the ciliary sulcus and the ciliary body, may be made of any suitable biocompatible material, which may be a metal such as platinum or a platinum alloy or a plastic such as PMMA or even any of the materials of which the bag-like or ring-like structure can be made.

In practice, a satisfactory degree of fixation of the implanted structure may be achieved by having the straight spines merely penetrate into the ciliary body without perforating and passing entirely through the sclera. In such a case, the spine length may be somewhat less than the thickness of the sclera. Alternatively, however, the surgeon may opt for a more positive anchoring of the implanted structure by providing the spines with bent-over hook-like distal end portions which may be positioned either internally of the sclera so as to be buried between the scleral tissues or externally of the sclera so as to be confined between the outside surface of the sclera and the surrounding sheath of the eyeball (Tenon's capsule). For the purposes of such an anchoring, the spines will initially be somewhat longer, by about 1.5–2 mm, than the thickness of the sclera. Thus, once the spines have been forced through the scleral tissues and the distal end regions of the spines have appeared in the spaces formed between the outside surface of the sclera and the surrounding sheath of the eyeball (Tenon's capsule) where the latter has been separated from the sclera, the surgeon will then proceed as follows: either the surgeon will make an incision into the sclera at each location where a hook-like portion of a respective spine is to be buried and after snipping off and removing the excess length of each such spine extending beyond the incision will bend the remaining distal end region of each shortened spine transversely to the body of that spine within the spread-apart incision so as to form the desired hook-like anchor portion, after which the incision will be closed; or the surgeon will bend the distal end region of each spine projecting past the outside surface of the sclera transversely to the body of that spine so as to form a hook-like portion lying flush against the adjacent portion of the outside surface of the sclera, after which the sheath of the eyeball is released to confine the hook-like anchor portions of the spines between the sclera and Tenon's capsule.

It should be pointed out, in this connection, that apart from providing the requisite fixation of the implanted structure, the use of a plurality of spines as aforesaid which penetrate or perforate the ciliary body also provides the implanted structure with the additional capability of accommodation upon contraction or relaxation of the ciliary muscle. As has already been mentioned, in a case where only fixation is a desideratum, the provision of three spines distributed at 90° spacings from each other over one half the circumference of the ring- or bag-shaped structure is deemed to be adequate and is currently preferred, although as few as two and as many as four or more spines would appear to be satisfactory as well. However, in a case where accommodation is a desideratum along with fixation, for purposes of dynamic balance it would be advantageous and is currently preferred to provide at least four and possibly as many as eight spines on the implantable structure distributed uniformly around the full circumference of the structure, although here too it appears that even more than eight or as few as two or three equiangularly distributed spines might be satisfactory as well.

Where, on the other hand, only a residual circumferential portion of the original capsular bag, consisting of the equatorially connected anterior and posterior capsular flaps (with or without a residual torn posterior capsule) and supported by the ciliary zonules, remains in the patient's eye after an ECCE, the artificial bag- or ring-like "spare parts" according to the present invention can be implanted in the region of the ciliary sulcus and retained securely in place without the use of spines as aforesaid. This is possible because the said residual portion of the capsular bag and the associated zonules underlie and thereby provide a support for the artificial ring- or bag-like structure and prevent it from falling into the vitreous humor. In any event, for the purposes of a ciliary sulcus mounting, the outer diameter of the spineless artificial ring- or bag-like structure will usually be somewhat larger than the outer diameter of the patient's natural capsular bag, for example, on the order of between about 13.5 and 14.5 mm and preferably about 14 mm so as to fit tightly against the ciliary sulcus. The diameter of the implant may nevertheless be somewhat smaller or larger than indicated, depending on whether an unusual eye size is encountered; for example, the diameter of the implant may be smaller than 13.5 mm for a hyperopic patient and larger than 14.5 mm for a highly myopic patient. Alternatively, however, the implantable ring- or bag-like structure may have an outer diameter of only about 10.5 mm (as does such a structure which is designed for implantation into the residual natural capsular bag), but in that case it is necessary to provide the structure with external loops or equivalent elements in the nature of haptics (not shown) adapted to press against the ciliary sulcus for stabilizing the implant. Such haptics should, therefore, be dimensioned to impart to the implantable structure an effective outer diameter, measured between the respective high points of the opposed haptics, of between about 13.5 and 14.5 mm and preferably about 14 mm.

In accordance with yet further embodiments of the present invention, it is contemplated that an artificial ring-like structure of the class described may have a split washer-like configuration, either as a closed-circle structure having telescoping opposite end regions, with one end region of the toroidal ring being slidably received in the channel-shaped opposite end region of the ring, or as an open-circle structure with the two opposite end regions being separated from one another by a circumferential gap. Such a ring thus will be circumferentially compressible to facilitate its implantation either into the region of the ciliary sulcus or into a residual capsular bag and will thereafter be able, when released and attempting to return to its original form, to exert an expansive force on either the ciliary sulcus or the equatorial region of the bag, with fixation of the ring at the ciliary sulcus, though principally achieved by the expansive force of the ring, being augmented by a series of external spines penetrating into the sclera or ciliary body to help keep the ring from dropping into the vitreous humor. A circumferentially compressible, toroidal, closed-circle ring structure may, furthermore, also incorporate some of the additional features of the rings mentioned previously, namely, anterior and posterior wall portions of the same or different radial widths, tool-engageable holes or depressions (indentations) in the upper and/or lower walls, and internal equatorial ribs. On the other hand, whereas a circumferentially compressible, open-circle ring structure may be toroidally hollow in form, i.e., internally grooved, it may also be solid in form, i.e., shaped like a bar or rod which is cross-sectionally either flat (e.g., square or rectangular) or round (e.g., circular or oval) and is devoid of an interior groove. It should be understood, in this regard, that the closed-circle, circumferentially compressible, toroidal ring-like structure can serve not only as a means for reinforcing a residual natural capsular bag around its entire periphery and for preventing collapse of the bag, but also as a full receptacle in either the bag or the ciliary sulcus for an IOL or other device to be implanted therein and as a means for inhibiting posterior capsular opacification of the bag, whereas the open-circle, circumferentially compressible ring-like structure when inserted into a capsular bag is primarily intended to stretch and keep the bag expanded to prevent its collapse (e.g., in case of pseudoexfoliation of the lens capsule if some of the ciliary zonules are torn or weakened), although such a ring if of toroidal or grooved form could also serve as a partial receptacle for an IOL or other implanted device in or out of the bag.

In accordance with another refinement of the present invention it is contemplated that the various "spare parts" disclosed herein will, whenever made from a soft absorbent material such as hydrogel, have the ability to absorb various solutions to treat different conditions. Thus, merely by way of example, "spare parts" that are designed to prevent posterior capsule opacification might be impregnated or soaked in an antimitotic solution such as 5-fluorouracil or mitomycin to specifically kill epithelial cells that reside in the equator of the capsular bag. Such "spare parts" may also be soaked or impregnated with antibiotics for the prevention of infections such as endophthalmitis, or with other drugs for the treatment of HIV related infections of the eye. Moreover, steroids can also be absorbed by "spare parts" made of these soft absorbent materials, enabling the surgeon to treat patients who have a history of iritis or uveitis during the post-operative period.

Generally speaking, therefore, the present application discloses a "spare part" which is designed for use by a surgeon for surgical implantation into either the residual natural capsular bag or the ciliary sulcus of a patient's eye following an extracapsular or intracapsular cataract extraction. Such a "spare part" comprises a body made of a biocompatible sheet material preformed into the shape of an artificial either anteriorly incomplete and posteriorly complete or both anteriorly and posteriorly incomplete capsular bag-like structure, the artificial capsular bag-like structure having a peripheral generally toroidal ring-shaped equatorial region and including an annular anterior wall and an either annular or circular posterior wall connected to each other at their radially outwardmost peripheries and jointly defining between the walls a channel-shaped compartment for receiving an implantable optical, mechanical or combined optical and mechanical device. At least one of the walls is provided on its respective anterior surface with means visually perceptible by the surgeon within the patient's eye, after the artificial capsular bag-like structure has been inserted into the patient's eye, to facilitate the proper manipulation and orientation of the artificial capsular bag-like structure within the patient's eye or of the optical and/or mechanical device when it is received in the compartment of the artificial capsular bag-like structure.

BRIEF DESCRIPTION OF THE DRAWINGS

The foregoing and other objects, characteristics and advantages of the present invention will be more clearly comprehended from the following detailed description of various embodiments of the invention when read in conjunction with the accompanying drawings, which are basically schematic or diagrammatic in nature and should be viewed as such, in which:

FIGS. 8 and 8A are both sectional views taken along the line 8—8 in FIG. 7, with FIG. 8 showing the radially wider posterior wall as being substantially parallel to the radially narrower anterior wall while FIG. 8A shows the larger posterior wall as being inclined posteriorly somewhat, at an angle of about 10°–15°, relative to the equatorial plane of the ring as well as to the plane of the narrower anterior wall thereof;

Figure 1:
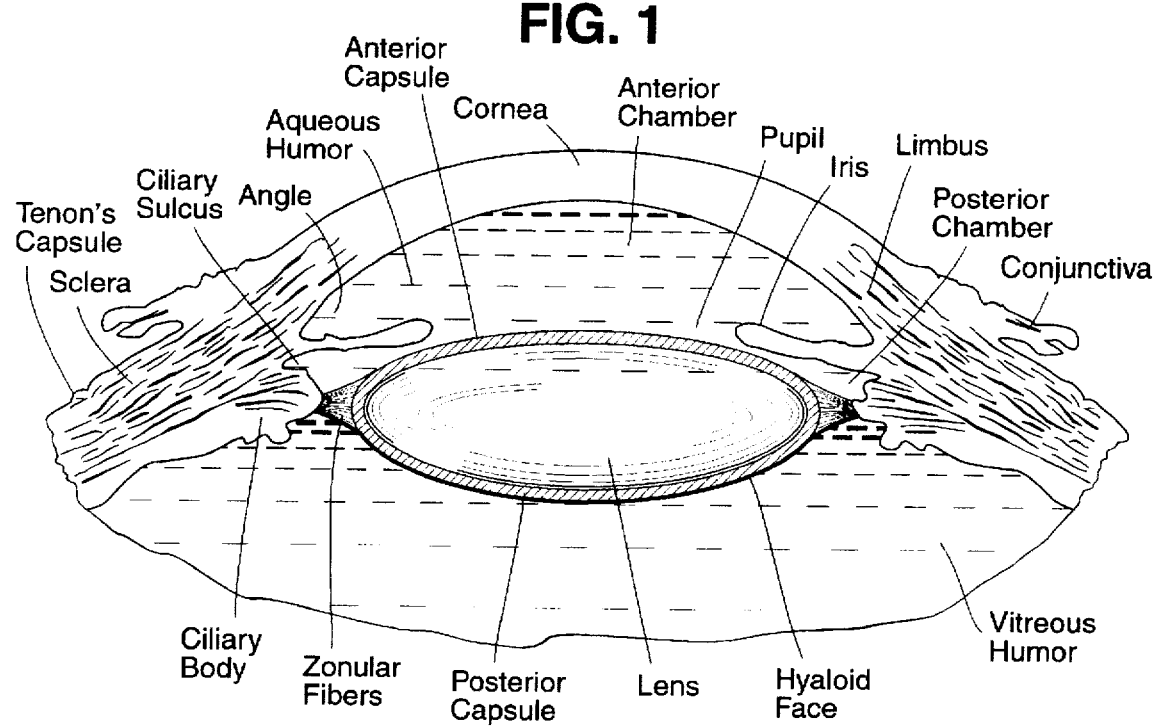
FIG. 1, which has already been discussed previously herein, is an axial section taken through a normal human eye, independent of any particular surgical procedure to be performed thereon, and is intended merely to identify, for purposes of reference, the various components of the eye which are pertinent to an understanding of the present invention.
Figure 4:
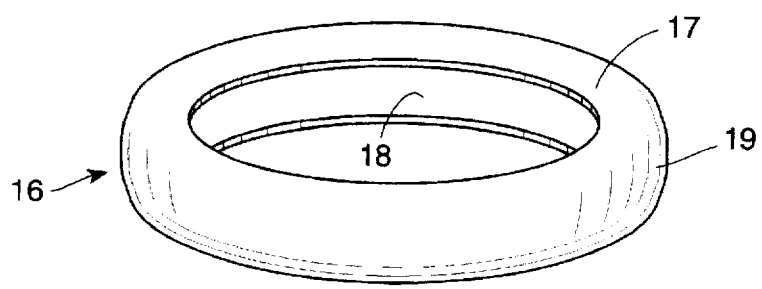
FIG. 4 is a perspective illustration of a generally toroidal ring-shaped structure in the form of a both anteriorly and posteriorly incomplete capsular bag-derived structure having annular anterior and posterior capsular flap-like walls in accordance with the basic principles of the present invention and constituting a basic "spare part" suited for implantation in either the capsular bag or the ciliary sulcus of the patient's eye.
Figure 6:
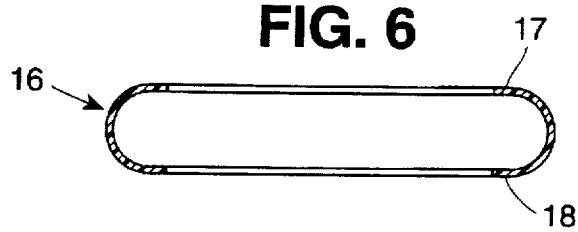
FIG. 6 is a sectional view taken along the line 6—6 in FIG. 5.
Figure 8:
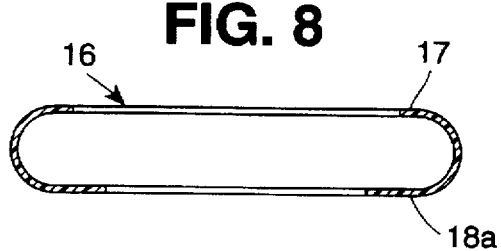
Figure 8A:
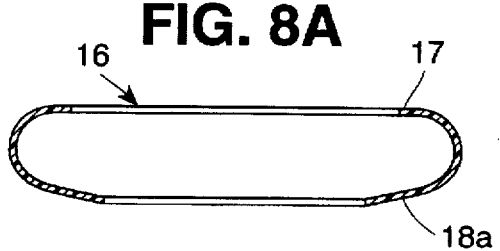
Figure 9:
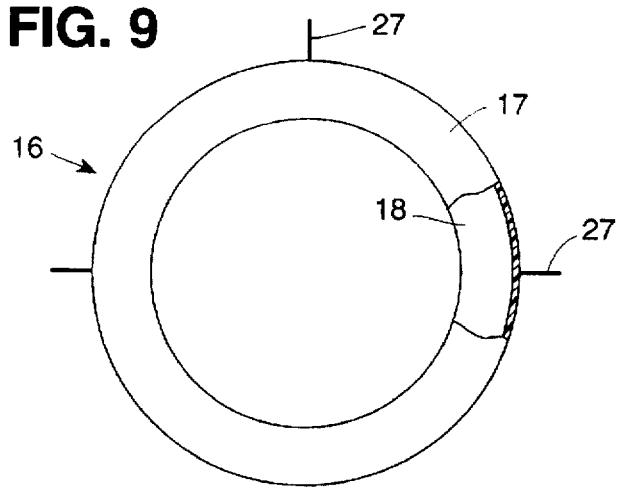
FIGS. 9 and 10 are plan views, similar to FIGS. 5 and 7, respectively, of the ring-shaped structure shown in FIG. 4 but illustrate the same as being provided, for purposes of a ciliary sulcus mounting, with a plurality of outwardly directed radial spines thereon.
Figure 10:
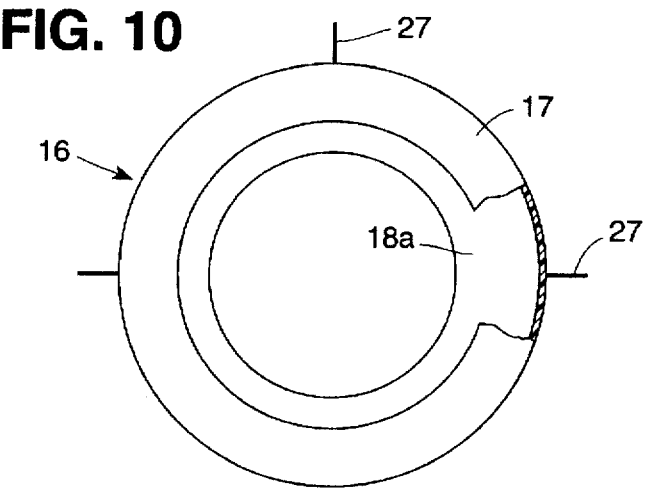
Figure 11:
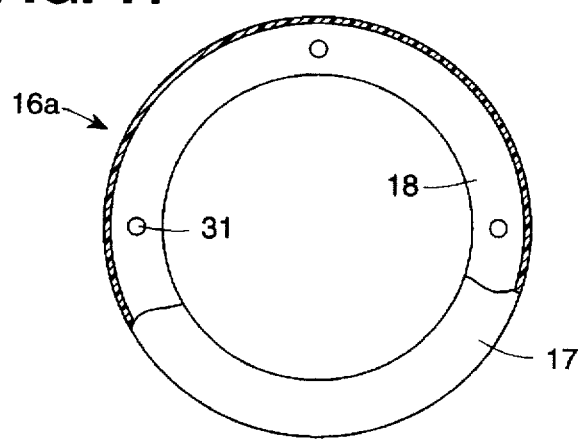
FIG. 11 is a plan view, similar to FIG. 5, of the ring-shaped structure shown in FIG. 4 but illustrates the same as being provided within one of the walls thereof with a plurality of holes or depressions for facilitating manipulation and rotational adjustment of the ring.
Figure 14:
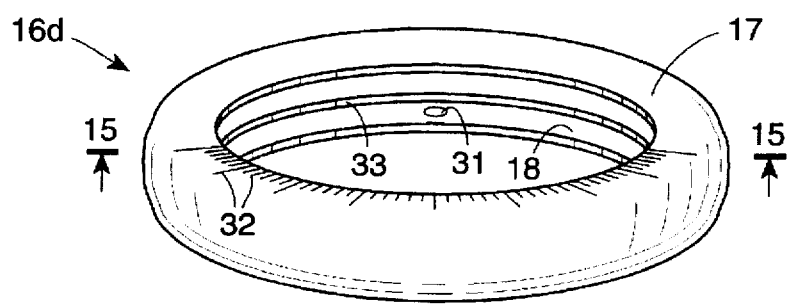
Figure 18:
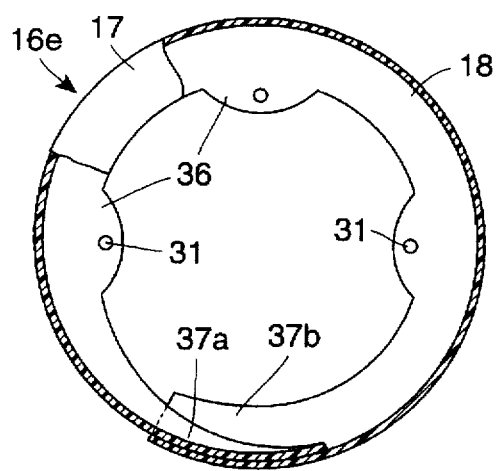
Figure 19:
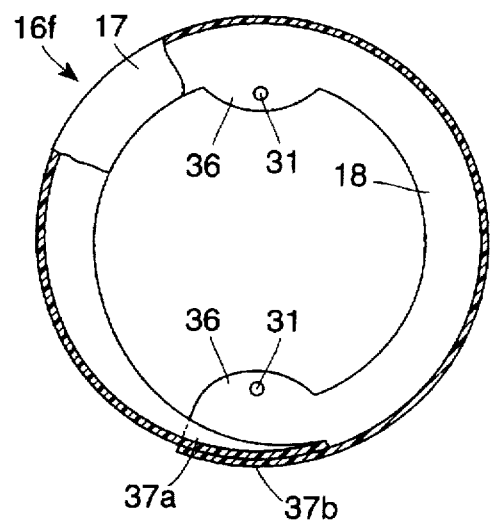
Figure 20:
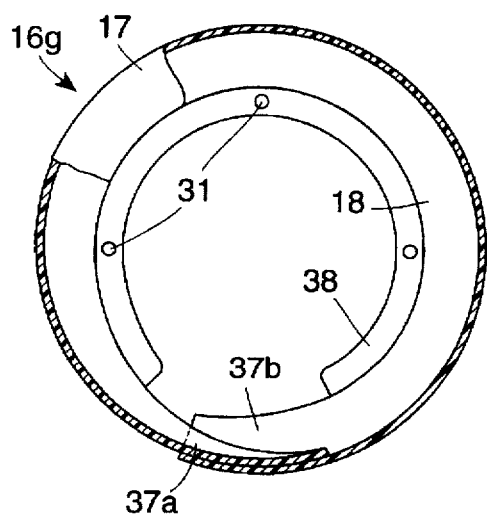
Figure 21:
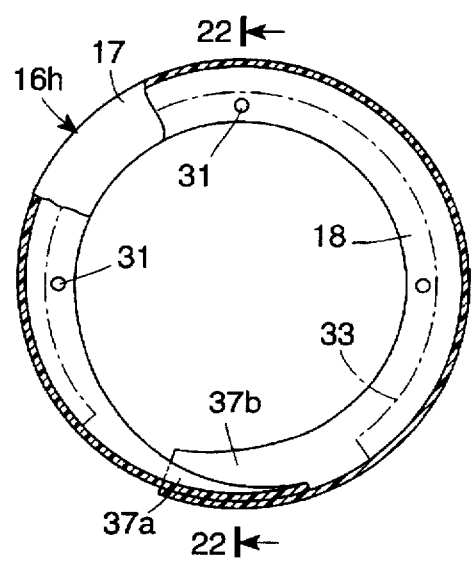
Figure 22:
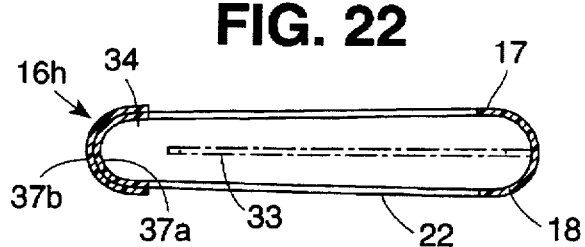
Figure 23:
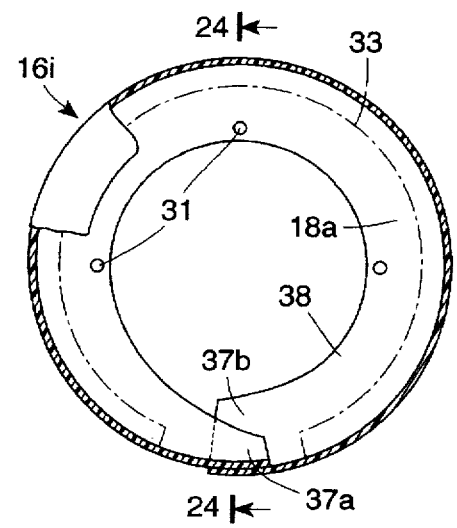
Figure 25:
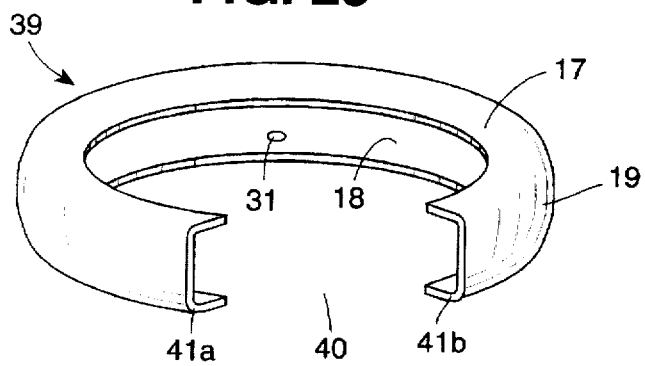
Figure 24:
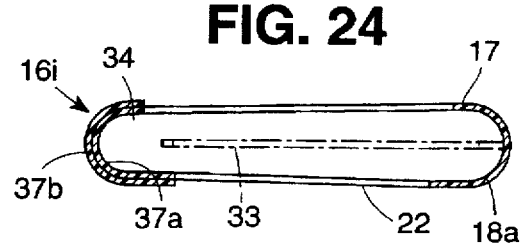
Figure 26:
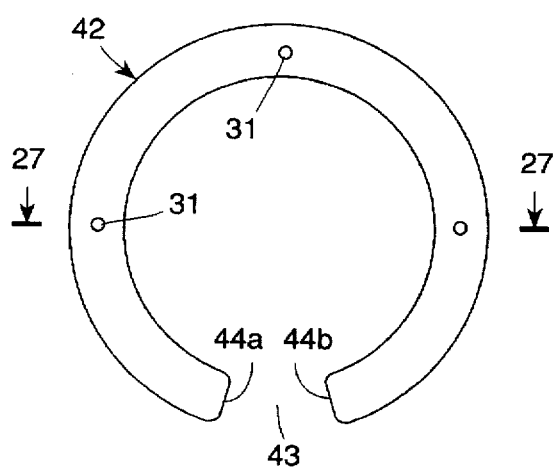
Figure 27:
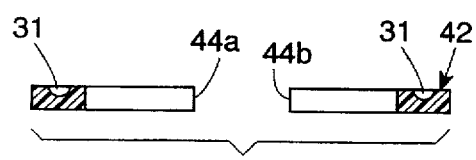
Figure 27A:
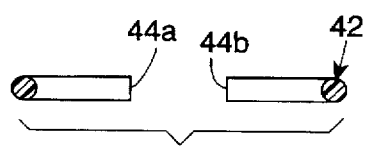
Figure 28:
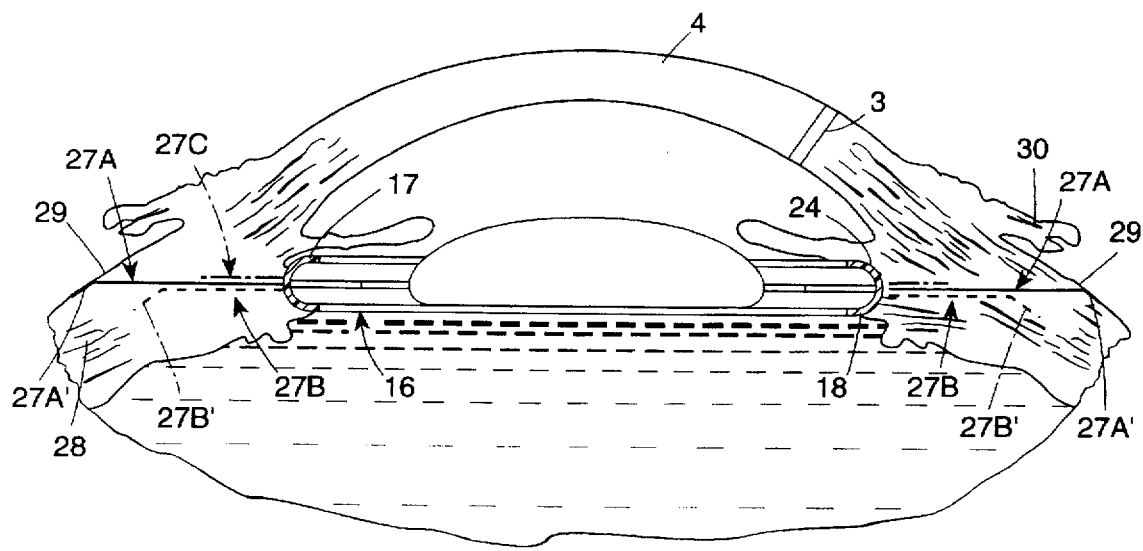
Figure 29:
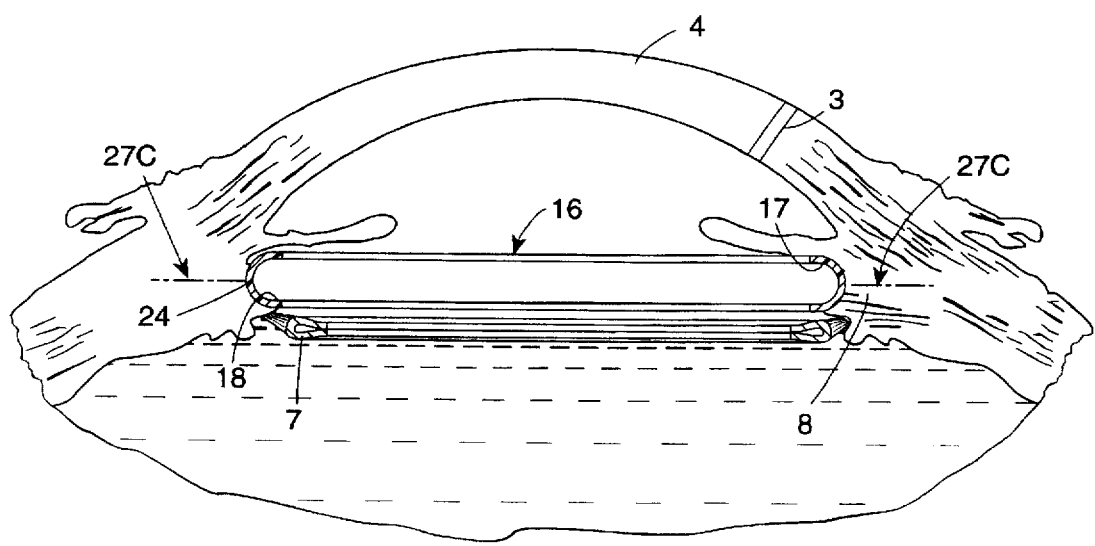
Figure 30:
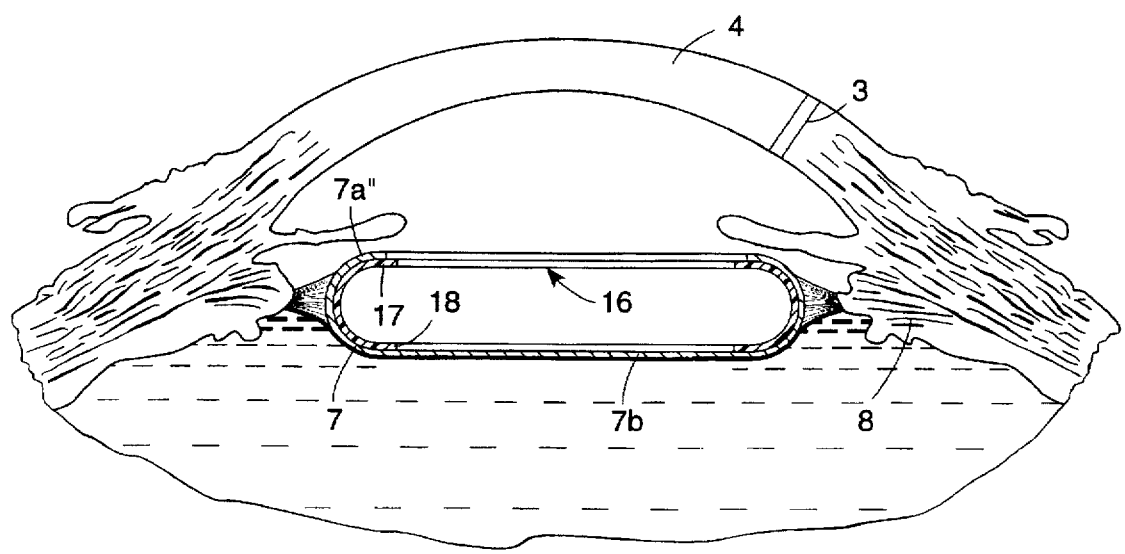
Figure 31:
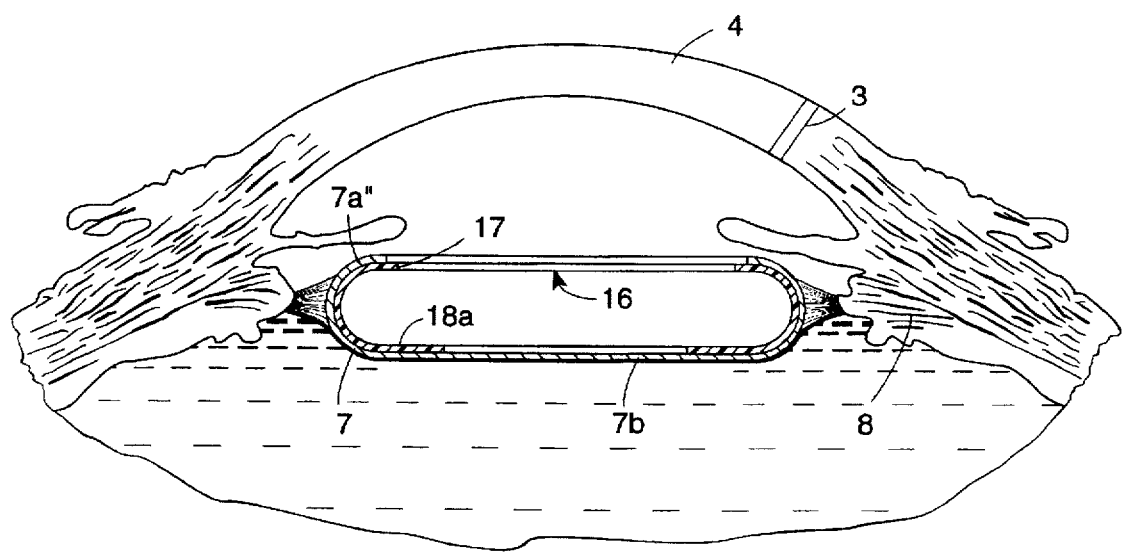
Figure 32:
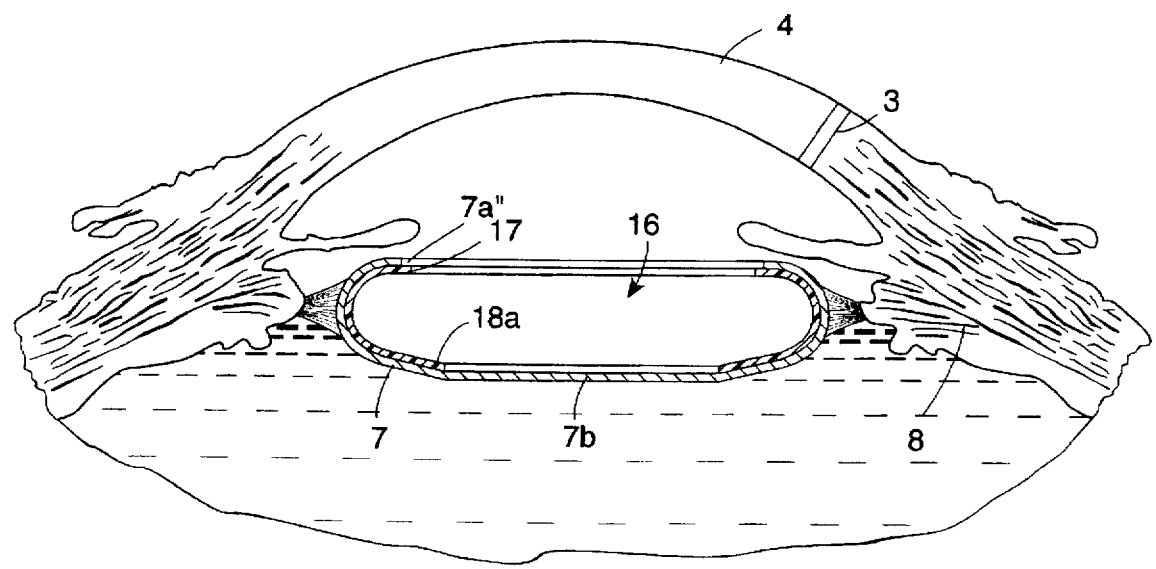
Figure 33:
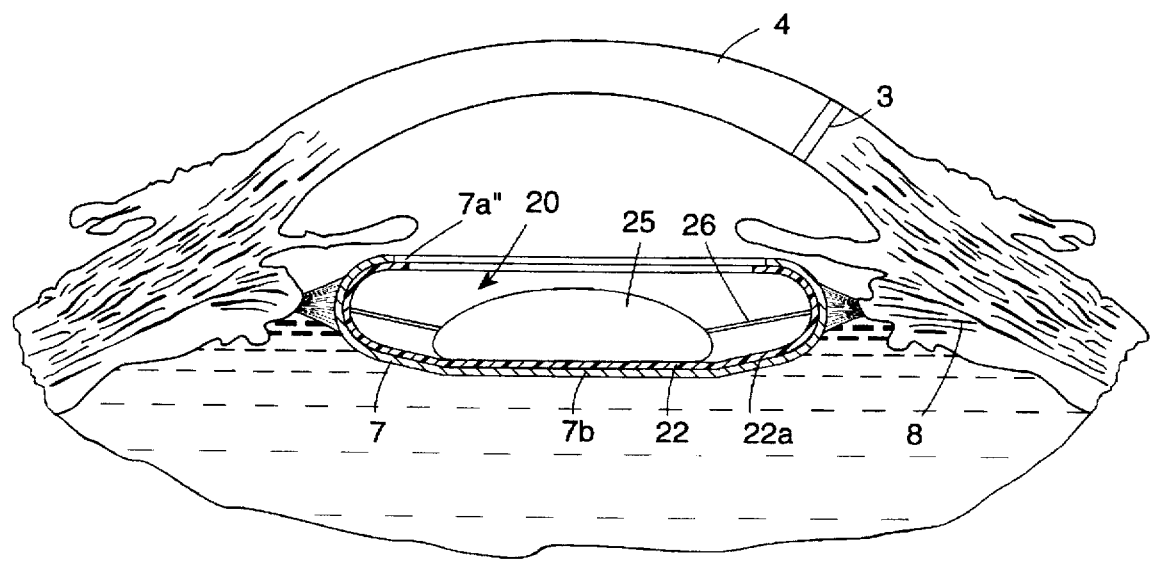

in its lower or posterior wall for facilitating manipulation/ adjustment of the structure by the surgeon and a set of degree markings on its upper or anterior wall for facilitating the required proper orientation of the axis of an implanted cylinder lens used for astigmatism correction;

FIG. 14 is a perspective illustration of a ring-shaped structure like that of FIG. 4 but provided with an interior equatorial rib which effectively defines two separate receptacles or compartments for different lenses, the structure being further shown as provided with an optional series of degree markings on its upper or anterior wall as well as an optional set of holes or indentations on its lower or posterior wall;

FIGS. 15, 15A and 15B are sectional views, similar to FIGS. 6, 8 and 8A, respectively, taken on the line 15—15 in FIG. 14;

FIG. 16 is a perspective illustration, similar to FIG. 14, of an anteriorly incomplete but posteriorly complete capsular bag-like structure having an interior circumferential rib and an optional series of degree markings on the anterior capsular flap-like portion;

FIGS. 17 and 17A are both sectional views taken along the line 17—17 in FIG. 16, with the structure of FIG. 17 being shown as having upper and lower walls substantially parallel to each other and to the equatorial plane of the structure, while the structure of FIG. 17A is shown as having the outwardmost peripheral portion of its lower posterior capsule-like wall angled posteriorly relative to the equatorial plane of the structure;

FIGS. 18, 19 and 20 are plan views of ring-shaped structures according to further modifications of the present invention which are provided with walls of equal radial widths and are circumferentially compressible by virtue of having a split ring-like configuration with one end portion telescoping slidably into the other end portion, the various rings differing from one another by being provided with different numbers of tabs or platforms which project inwardly from one of the walls (preferably the lower or posterior wall) and have respective holes or depressions therein for facilitating manipulation of the rings;

FIG. 21 is a plan view, similar to FIGS. 18, 19 and 20, of a circumferentially compressible split ring-shaped structure with equal-width walls which has no platforms or tabs but rather has the desired number of holes or depressions formed directly in the lower wall of the ring as in FIG. 11;

FIG. 22 is a sectional view taken along the line 22—22 in FIG. 21;

FIG. 23 is a plan view, similar to FIG. 21, of a circumferentially compressible split ring-shaped structure which has walls of unequal radial widths and has no platforms or tabs, with the holes or depressions being formed in the radially larger posterior wall of the ring;

FIG. 24 is a sectional view taken along the line 24—24 in FIG. 23;

FIG. 25 is a perspective illustration of an internally grooved split ring-shaped structure which in its toroidal form is basically similar to that shown in FIG. 4 but differs therefrom in being provided with a gap along its periphery to facilitate circumferential compression of the ring preparatory to its implantation;

FIG. 26 is a plan view of a solid bar- or rod-shaped grooveless circumferentially compressible split ring-like structure and shows the same as being optionally provided with holes or depressions therein;

FIGS. 27 and 27A are both sectional views taken along the line 27—27 in FIG. 26 and illustrate the body of the grooveless split-ring structure as being optionally either flat or round in cross-section;

FIG. 28 is a section through the eye, similar to FIG. 1, and illustrates an artificial toroidal ring-shaped structure according to the present invention implanted into the ciliary sulcus region of the eye following an intracapsular cataract extraction, the ring being shown anchored in place by external spines such as shown in FIGS. 9 and 10, with the spines indicated by solid lines having hook-like distal end regions confined between Tenon's capsule and the sclera, with the spines indicated by broken dash-dash lines having hook-like distal end regions buried between the tissues within the body of the sclera, and with the spines indicated by broken dot-dash lines being merely straight and having no hook-like regions, and an intraocular lens being shown as having been inserted into the ring;

FIG. 29 is a view similar to FIG. 28 and likewise illustrates an artificial ring-shaped structure implanted into the ciliary sulcus region of the eye, but in this case the ring is located anteriorly of and is posteriorly supported in place by the post-ECCE residue of the natural capsular bag, with the fixation of the ring being assisted by a plurality of exterior hookless radial spines penetrating into the region of the sclera surrounding the ciliary sulcus;

FIG. 30 is a section through the eye, similar to FIG. 1, and illustrates an artificial toroidal ring-shaped structure with equal-width walls according to the present invention implanted into the residual natural capsular bag of the eye following an extracapsular cataract extraction;

FIG. 31 is a view similar to FIG. 30 and illustrates an artificial toroidal ring-shaped structure with unequal-width parallel walls implanted into the residual natural capsular bag;

FIG. 32 is a view similar to FIG. 31 and again illustrates an artificial toroidal ring-shaped structure with un-equal-width walls implanted into the residual natural capsular bag, but here with the lower posterior capsular flap-like wall of the structure angled posteriorly somewhat relative to the equatorial plane of the ring; and FIG. 33 is a view similar to FIG. 32 and shows an artificial posteriorly complete capsular bag-like structure implanted into the residual natural capsular bag, the implanted bag-like structure having a configuration similar to that of the ring-like structure shown in FIG. 32 and being shown as having an IOL received therein.

DETAILED DESCRIPTION OF THE INVENTION

Figure 2:
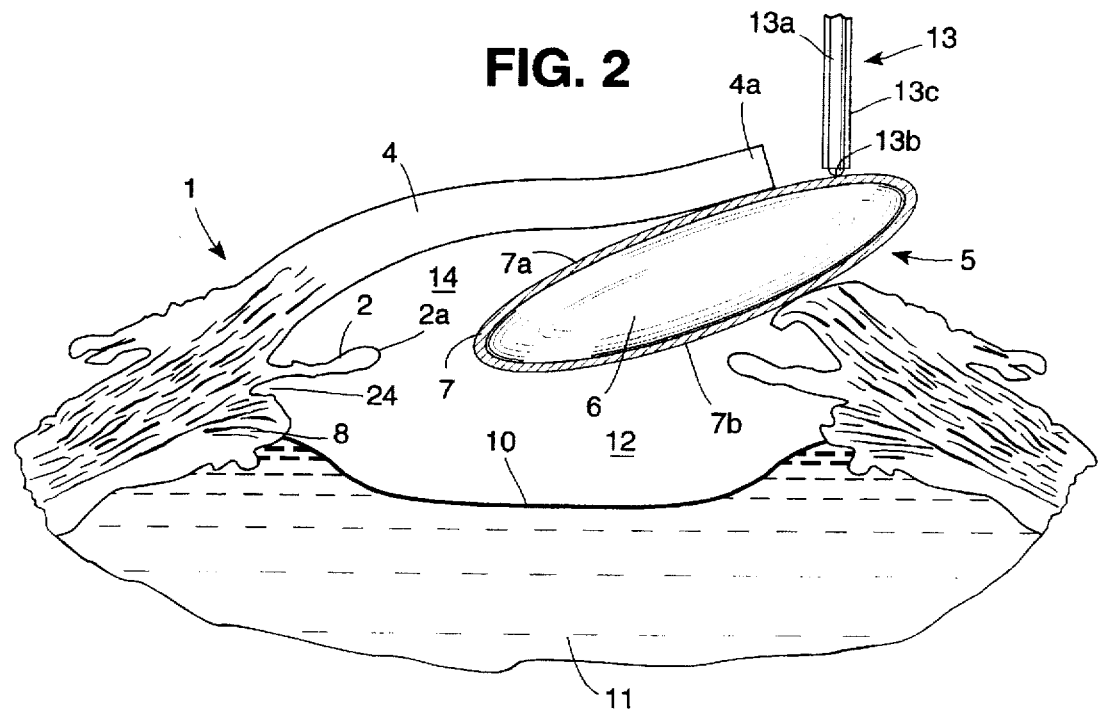
FIG. 2 is a similar section through an eye and illustrates the lens removal stage of an intracapsular cataract extraction (ICCE) in progress.
Figure 3:
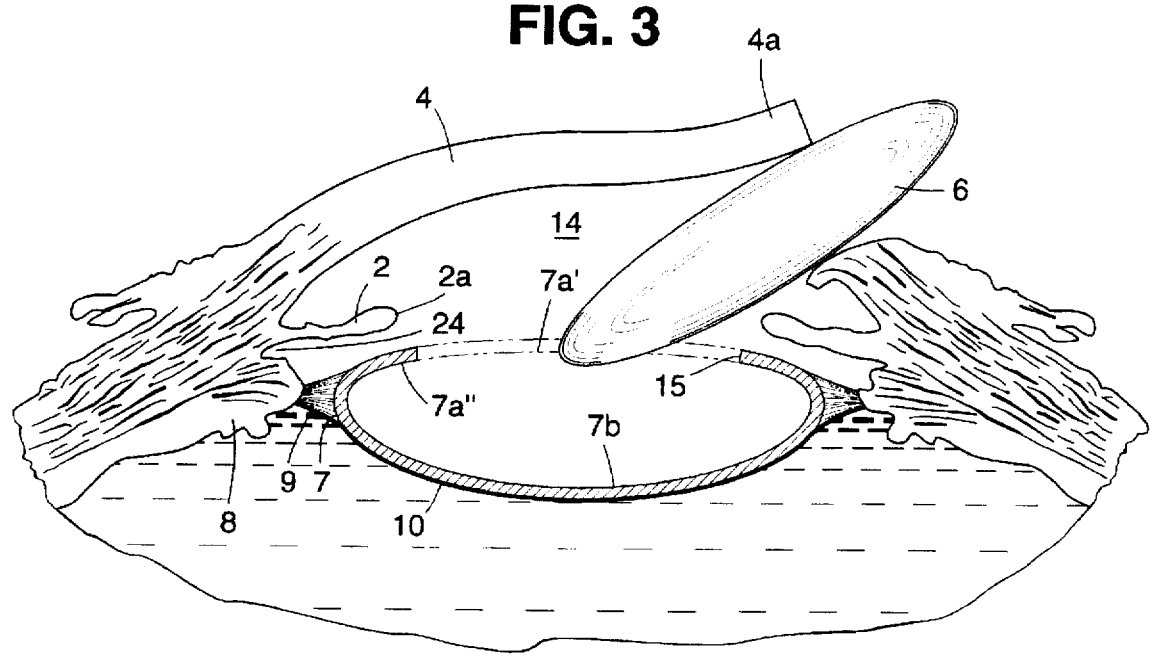
FIG. 3 is a view similar to FIG. 2 and illustrates the lens removal stage of an extracapsular cataract extraction (ECCE) in progress.

Referring now to the drawings in greater detail, an ICCE and an ECCE in progress are shown, merely by way of example and as background information only, in FIGS. 2 and 3, respectively. As is well known and, consequently, has not been explicitly illustrated, in each of the two operations the eye 1 is first subjected to a conventional preparatory treatment during which the eye is anesthetized with a topical anesthetic or with a retrobulbar or peribulbar block and the iris 2 is treated to dilate the pupil 2a, following which an appropriate incision 3 is made in the cornea 4 along one section of the perimeter thereof, i.e., just anteriorly of the limbal region, so that the resultant corneal flap 4a can be lifted sufficiently to provide the surgeon with the requisite degree of access to the interior of the eye. The dilation of the pupil 2a provides the maximum possible exposure of the lens 5 which consists of the nucleus 6, the cortex (not shown) and the enveloping capsular bag 7 therefor constituted by the peripherally (equatorially) joined anterior capsule 7a and posterior capsule 7b. The lens 5 is initially attached along its entire periphery to the ciliary body 8 by zonular fibers 9, and normally the posterior capsule 7b is in full surface contact with the hyaloid face 10 of the vitreous humor 11, as shown in FIG. 1.

Turning now in particular to FIG. 2, in the case of the intracapsular cataract extraction the surgeon, after the incision has been made, first injects a suitable enzyme, e.g. an alpha-chymotrypsin, into the posterior chamber 12 to dissolve the zonular fibers 9 around the entire periphery or equatorial zone of the endogenous capsular bag 7, thereby to disconnect the lens 5 from the ciliary body. With the corneal flap 4a then appropriately held back, the surgeon inserts the end region of a low-temperature probe 13 (conventionally a thin metal rod 13a covered entirely except for its tip 13b by an insulating sheath 13c) into the eye through the incision 3, the anterior chamber 14 and the pupil 2a to bring the tip of the probe into contact with the anterior capsule 7a of the lens. This causes the portion of the anterior capsule at the contact location and a small region of the lens nucleus under and around the contact location to freeze and thereby to adhere to the tip of the probe, whereupon the lens is loosened from the hyaloid face 10 and is then lifted bodily out of the eye. (Of course, the removal of the cataract in an ICCE procedure can also be effected by other suitable techniques not necessary to describe in detail herein, for example, any of the various techniques for this purpose which were well known before the "freeze" method was developed.)

In the case of the extracapsular cataract extraction (FIG. 3), on the other hand, after the corneal incision has been made, the zonular fibers 9 are not touched. Rather, a major interior portion 7a' of the anterior capsule 7a, which portion is shown only in phantom outline in FIG. 3 and is the portion located just behind the dilated pupil 2a, is cut away along a generally circular locus 15 substantially coinciding with (albeit slightly smaller than) the expanse of the dilated pupil. It will be understood, therefore, that after the severed portion 7a' of the anterior capsule has been removed, the endogenous capsular bag 7 is still located in the eye but only in an anteriorly incomplete form, i.e., consisting of the posterior capsule 7b and the residual, equatorially connected, annular anterior capsular flap 7a". Thereafter, the lens nucleus 6 is expressed from the residual capsular bag by conventional techniques well known in the art, which may entail the use of a muscle hook and a lens loop (not shown) aided, if deemed appropriate by the surgeon, by an injection of viscous sodium hyaluronate into the residual capsular bag to enable the lens nucleus to be floated out of the bag through the pupil and into the anterior chamber, or which may as an alternative entail the use of phacoemulsification to break up and emulsify the nucleus preparatory to its removal from the eye (in this alternative, of course, the nucleus would not have the cohesive form shown in FIG. 3 but would be amorphous). In either procedure, the removal of the nucleus is followed up by removal of the cortex through irrigation and aspiration.

It should be kept in mind, in regard to the herein set forth descriptions of the two types of cataract extractions, that FIGS. 2 and 3 (and for that matter all the other figures of the drawings) are purely diagrammatic illustrations the purpose of which is to facilitate an understanding of those procedures and of the still to be described principles and embodiments of the present invention. The illustrations are not intended to represent in precise detail the various aspects of the physiological structures and surgical techniques involved in the two operations.

More particularly, one version of the basic "spare part" accordingly to the present invention, which an ophthalmic surgeon will have available to him (essentially in the manner described in the aforesaid U.S. Pat. No. 4,888,016) for use in connection with an implantation of an IOL or other optical, mechanical or combined optical/mechanical device into a patient's eye as a follow-up to either an ICCE or an ECCE, is shown in FIG. 4 as being a generally toroidal ring-like structure 16 having an annular upper wall 17 and an annular lower wall 18 connected to each other equatorially, i.e., along the outer periphery 19, of the ring 16. A second version of the basic "spare part" according to the present invention is shown in FIG. 4A as being a structure 20 generally similar to the ring 16 in that it has an upper wall 21 and a lower wall 22 connected to each other equatorially, i.e., along the outer periphery 23, of the structure 20, the sole difference between the two structures being that in the structure 20, although the upper wall 21 thereof is annular and identical to the upper wall 17 of the structure 16, the lower wall 22 of the structure 20 is not annular but rather is essentially circular and extends fully, i.e., without a medial opening, across the entire lower expanse of the structure 20.

Referring now for the moment to FIGS. 2 and 3, it can be seen that the structure 16 in essence resembles the capsular bag 7 shown in FIG. 2 with the middle regions of both the anterior capsule 7a and the posterior capsule 7b cut away in the manner represented in phantom outline for the anterior capsule at 7a' in FIG. 3. For purposes of identification, therefore, the toroidal ring-like structure 16 will herein occasionally be referred to an artificial both anteriorly and posteriorly incomplete capsular bag-like or capsular bag-derived structure, with the upper wall 17 constituting an anterior capsular flap-like portion and with the lower wall 18 constituting a posterior capsular flap-like portion. On the other hand, it can likewise be seen that the structure 20 in essence also resembles the capsular bag 7 shown in FIG. 2 but with only the middle region of the anterior capsule 7a cut away in the manner represented at 7a' in FIG. 3. For purposes of identification, therefore, the structure 20 will herein occasionally be referred to as an artificial anteriorly incomplete but posteriorly complete capsular bag or capsular bag-like structure, with the upper wall 21 constituting an anterior capsular flap-like portion and with the lower wall 22 constituting a posterior capsule-like portion.

Figure 5:
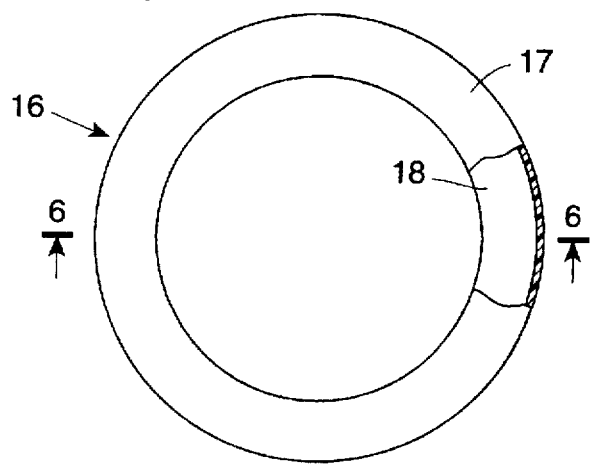
FIG. 5 is a plan view of the ring-shaped structure shown in FIG. 4, with a part of one wall (here the upper or anterior wall) being broken away, and illustrates the structure as having walls of substantially equal radial dimensions (as measured from the equatorial region of the ring)
Figure 7:
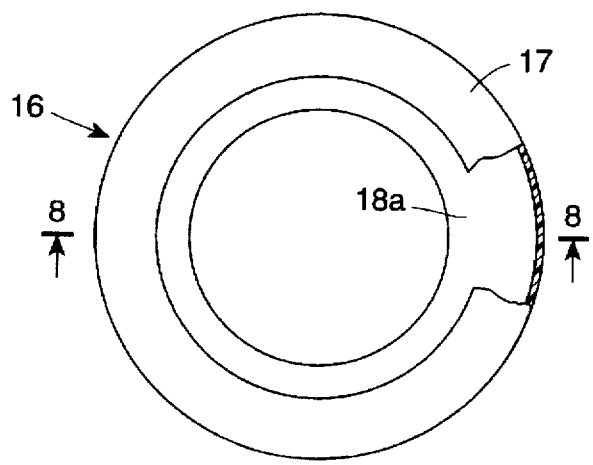
FIG. 7 is a plan view, similar to FIG. 5, of the ring-shaped structure shown in FIG. 4 but here illustrating the same as having annular anterior and posterior walls of unequal radial dimensions.

In the basic form of the toroidal ring structure 16, the upper and lower, i.e., the anterior and posterior, walls 17 and 18 thereof are substantially parallel to each other and the equatorial plane of the ring, and their radial widths, as measured from and in the plane of the equatorial periphery 19 of the ring, are substantially equal, as is best shown in FIGS. 5 and 6. In a first alternative version of this "spare part," the radial widths of the two parallel walls may also be unequal, with the lower or posterior wall 18a, for example, being wider than the upper or anterior wall 17 as shown in FIGS. 7 and 8, while in a second alternative version the wider lower wall 18a may also be inclined somewhat, e.g., at an angle of between about 10° and about 15°, posteriorly relative to the equatorial plane of the ring and the plane of the narrower upper wall 17 as shown in FIG. 8A. The ring structure 16 according to any of these variants can be implanted directly into the patient's residual capsular bag 7, as shown in FIGS. 30, 31 and 32, respectively, and it can also, even without structural modification, be implanted in the ciliary sulcus 24, as shown in FIG. 29, as long as at least the peripheral portion of the natural capsular bag 7 and its ciliary zonule 9 still remain in the patient's eye to provide support for the ring 16 and any IOL or other device inserted therein sufficient to prevent the implanted ring and/or other device from falling into the vitreous humor. Implantation of the ring 16 in the residual capsular bag is, of course, to be preferred, if at all possible, not only because that provides the best way of preventing the ring and any device therein from falling into the vitreous humor, but also because, by virtue of the hereinbefore mentioned dimensional relationship between the equatorial diameters of the ring and the bag and by virtue of the resultant full surface contact between, on the one hand, the equatorial regions of the ring and the bag and, on the other hand, the lower wall 18 or 18a of the ring and the outermost peripheral region of the posterior capsule 7b, the bag is prevented from shrinking, decentration of the implanted ring and any subsequently inserted IOL or other device is effectively avoided, and posterior capsular opacification is inhibited.

Figure 4A:
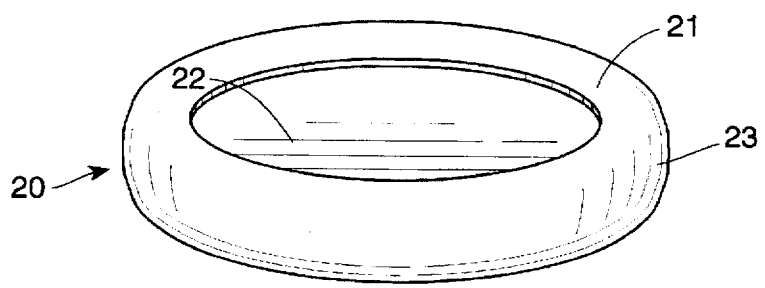
FIG. 4A is a perspective illustration, similar to FIG. 4, of an anteriorly incomplete but posteriorly complete capsular bag-like structure having an annular anterior capsular flap-like wall and an imperforate full-size posterior wall in accordance with the principles of the present invention and likewise constituting a basic "spare part" suited for implantation in either the capsular bag or the ciliary sulcus of the patient's eye.

It will be understood that the foregoing description, mutatis mutandis, applies equally to the artificial anteriorly incomplete but posteriorly complete capsular bag-like structure 20 shown in FIG. 4A. Thus, the structure 20 may have a full and imperforate lower or posterior capsule-like wall 22 the plane of which is parallel to the plane of the upper anterior capsular flap-like wall 21, as is shown in FIG. 17 for a similar structure 20a incorporating some other auxiliary features to be more fully described presently. Alternatively, the structure 20 may have a lower wall 22 which, as is shown in FIG. 17A for the mentioned structure 20a, has an outer peripheral region 22a the radial width of which is somewhat greater than the width of the upper wall 21 and which is inclined somewhat, e.g., at an angle of about 10°–15°, posteriorly relative to the plane of the upper wall and the equatorial plane of the structure, the inclined peripheral region extending from the equatorial region of the structure to the outer boundary of the mid-region of the lower wall which is generally parallel to the plane of the upper wall 21. Upon implantation of a bag-like structure 20 having an inclined peripheral region 22a into a patient's residual capsular bag 7 as shown in FIG. 33, an appreciably greater surface contact pressure will be exerted thereby on the posterior capsule 7b so as to provide an enhanced capsular opacification-inhibiting effect. This effect can be even further enhanced by implanting into the bag-like structure 20 an IOL 25 the haptics 26 of which, as also shown in FIG. 33, are correspondingly inclined anteriorly somewhat relative to the plane of the lens body, by virtue of which the forces acting on the IOL will ensure that the mid-region of the lower or posterior wall 22 of the artificial bag-like structure 20 is pressed firmly against the underlying mid-region of the natural posterior capsule 7b so as to inhibit the formation of Elschnig's pearls on the posterior capsule.

When the surgeon, after the performance of an ICCE, is faced with having to implant either a toroidal ring-like structure 16 (FIG. 4) or a capsular bag-like structure 20 (FIG. 4A) into a patient's eye in the region of the ciliary sulcus thereof because the eye has no remaining residue of the natural capsular bag in place, those structures, irrespective of their upper and lower wall configurations, cannot be used as they are because, as previously mentioned, means must be provided to anchor them to the sclera so as to prevent them from falling into the vitreous humor. To this end, in accordance with the present invention, the surgeon will have available to him or her a supply of "spare parts" of the various types disclosed herein which already have such anchoring means secured thereto. Such anchoring means, as shown in FIGS. 9 and 10 with respect to (merely as an example) a ring-like structure 16 having either equal-width walls 17 and 18 or unequal-width walls 17 and 18a, preferably consist of a plurality of sharp-pointed, relatively stiff but flexible spines 27 which are made of a suitable metallic or plastic biocompatible material and are secured to the exterior surface of the ring so as to project generally radially therefrom in the equatorial plane of the ring. It will be understood, of course, that the spines 27 can also be used in connection with the capsular bag-like structures 20 and 20a as well as with any of the other artificial ring-like and bag-like structures disclosed herein and still to be discussed. The manner in which such spines are used to anchor the implanted structures in place will be more fully described presently. In any event, while four such spines at equiangular spacings from each other circumferentially of such ring-like or bag-like structures would no doubt afford an adequately firm degree of fixation and even two might also be acceptable from that standpoint, it is preferred to provide three spines 27 spaced 90° from each other over one half of the circumference of the structure as shown and located, respectively, at the 3 o'clock, 9 o'clock and 12 o'clock positions. The material of which the spines are made, as previously indicated, may be either a metal (e.g., platinum or a platinum alloy or the like) or a plastic (e.g., PMMA or even any of those which the implantable structures are made).

Three alternative ways of effecting the fixation of a toroidal ring-like structure 16 to the sclera in the case of a ciliary sulcus mounting thereof in the absence of any residue of the original capsular bag are schematically illustrated in FIG. 28 (the procedure will be the same for a capsular bag-like structure 20 or 20a). As previously indicated, for this purpose the implantable "spare part" is provided with a plurality of radially outwardly extending spines (designated 27 in FIGS. 9 and 10).

Generally speaking, the affixation can be effected by means of primarily straight spines which perforate (extend into and entirely through) the sclera and have bent-over hook-like distal end regions buried exteriorly of the sclera between its outer surface and the overlying regions of Tenon's capsule—these spines are designated 27A and illustrated in solid lines in FIG. 28; or by means of primarily straight spines which penetrate (extend into but only partly through) the sclera and have bent-over hook-like distal end regions buried interiorly of the sclera between the scleral tissues—these spines are designated 27B and illustrated in dash-dash broken lines in FIG. 28; or by means of entirely straight spines which penetrate the sclera—these spines are designated 27C and illustrated in dot-dash broken lines in FIG. 28.

More particularly, for anchoring the implanted structure 16 exteriorly of the sclera, each spine 27A initially will have to be sufficiently long to be able to perforate the sclera, i.e., to penetrate through the entire thickness of the portion of the sclera 28 between the ciliary sulcus 24 and the conjunctiva 30 and to project beyond the outer surface of the sclera to the extent of about 1.5–2 mm. Prior to having caused the spines 27A to perforate the sclera, of course, the surgeon will have raised or separated the sections of Tenon's capsule 29 which overlie the perforated portions of the outer surface of the sclera from those surface portions (this separation is not expressly shown). Ultimately, therefore, the distal end regions 27A' of the spine extend into the spaces formed between Tenon's capsule and the sclera at those locations. The surgeon can then, using a suitable pair of forceps or like tool, bend the distal end regions 27A' of the spines 27A transversely and generally posteriorly of the main body portions of the spines, so that each bent-over end region effectively constitutes a hook-like element lying against the uncovered outer surface of the sclera. Upon release of Tenon's capsule, therefore, the hook-like distal end regions of the spines are confined between and locked in place by the sheath and the sclera, which prevents the implanted ring-like structure 16 from slipping out of the ciliary sulcus and falling into the vitreous humor.

Alternatively, for anchoring the implanted structure interiorly of the sclera, although in theory the spines 27B need not be as long as the spines 27A, as a practical matter it is found advantageous for the spines 27B to be initially also sufficiently long to be able to perforate the sclera and project beyond the outer surface of the sclera. Once the original distal end regions of the spines 27B are visible at the spaces between the outer surface of the sclera and the raised sections of Tenon's capsule, therefore, the surgeon, knowing the locations and orientations of the spines within the sclera, will be able to make a series of separate surgical incisions (not shown) in the sclera to render the mid-regions of the spines visible in the incisions. The surgeon can then cut the spines each in its respective incision, extract the severed end sections of the spines from the sclera, and bend the so newly formed distal end regions 27B' of the spines transversely to the main body portions of the spines into the respective spaces defined by the opened incisions. As a result, when the incisions are then closed again by the surgeon, the hook-like elements constituted by the spine end regions 27B' will be buried between and locked in place by the scleral tissues, which as in the previous case will prevent the implanted structure from slipping out of the ciliary sulcus and falling into the vitreous humor.

On the other hand, when an artificial ring- or bag-like structure according to the present invention, such as the structure 16, is to be implanted in the region of the ciliary sulcus of an eye following an ECCE where only a peripheral residue of the natural capsular bag 7 has remained in the eye, the residual equatorial portion of the natural bag (the anterior and posterior capsular flaps) and its associated ciliary zonule, as shown in FIG. 29, will constitute, apart from the pressing contact between the structure and the ciliary sulcus, an added support for the implanted structure for preventing it from dropping into the vitreous humor. In such a case, however, the surgeon may wish to use an implantable structure provided also with straight spines 27C which, upon penetrating into the sclera, will afford (without recourse to hook-like bent-over anchoring portions such as are provided on the spines 27A and 27B) an extra measure of safety against the possibility of the structure dropping into the vitreous humor.

From the description of the present invention so far, it will be clear that although ophthalmic surgeons are highly skilled practitioners, it may be desirable to provide means on or in conjunction with the "spare parts" to be implanted in patients'eyes for facilitating the manipulation of the implanted structures. One such surgical assistance means is shown in FIG. 11 which represents a ring-like structure 16a. This structure is for all practical purposes identical with the structure 16 shown in FIG. 5 but differs therefrom in that in one at least one of the walls 17 and 18 thereof, here shown only in the lower wall 18, there are provided several holes or indentations 31 (depressions). In the embodiment of the invention shown in FIG. 11, three holes or indentations are provided which are distributed at 90° spacings from each other over one half the circumference of the structure, but there is no constraint on the number or disposition of such holes or indentations; in other words, there may be more or less than three of them arranged at any suitable, preferably equiangular, spacings from one another, and the holes or indentations 31 could also be provided on the upper wall 17 (not shown). These holes or indentations, which will be visually perceptible to the surgeon during the implantation procedure, are intended to provide specified gripping locations to enable the surgeon, using an appropriate tool, to manipulate the implantable structure 16a into the proper position within the patient's eye, irrespective of whether the implantation site is the residual capsular bag or the ciliary sulcus.

Figure 12:
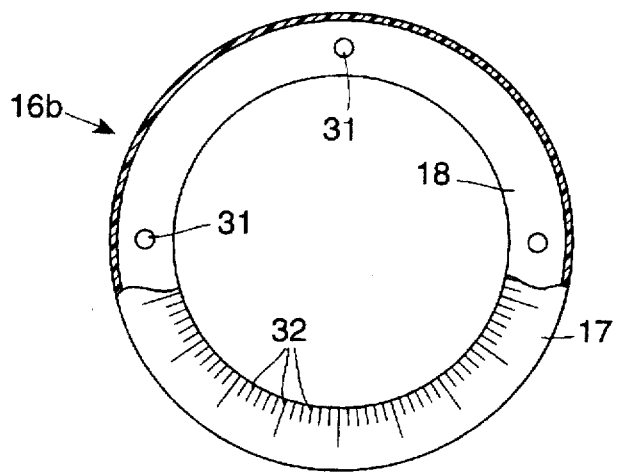
FIGS. 12 and 13 are plan views, similar to FIGS. 5 and 7, respectively, of the ring-shaped structure shown in FIG. 4 and illustrate the two embodiments as being provided with either or both of a set of holes or depressions (indentations)
Figure 13:
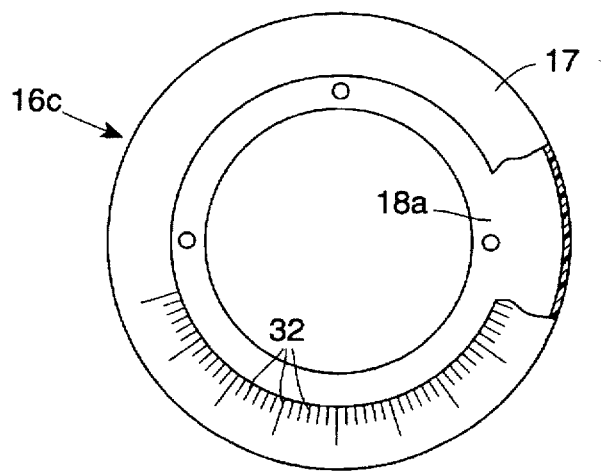

FIG. 12 shows a ring-like structure 16b which is again essentially identical to the structure 16 shown in FIG. 5 but which is provided not only with holes or indentations 31 in the lower wall 18 but is also provided on the upper wall 17 with a series of degree markings 32 at suitable angular spacings from each other. In FIG. 12, the degree markings are shown as distributed uniformly over one half the circumference of the ring at 5° spacings, but the markings could be distributed over the full circumference of the ring and at uniform angular spacings of more or less than 5°. The visually perceptible degree markings are intended to facilitate the insertion into the implanted structure of a cylinder lens or a toric lens for astigmatism correction, with the degree markings enabling the surgeon to achieve a proper orientation of the axis of the lens. It should be understood, however, that in the ring-like structure 16b of FIG. 12 the presence of the holes or indentations 31 is an optional feature, in other words, that FIG. 12 is not intended to specify that both the series of degree markings on the upper wall and the series of holes or indentations on the lower wall must be present at the same time in the same structure. The same holds true for the ring-like structure 16c shown in FIG. 13 which differs from the structure 16b of FIG. 12 only in that the lower wall 18a is radially wider than the associated upper wall 17.

FIG. 14 shows a ring-like structure 16d which is essentially identical to the structure 16b shown in FIG. 12 but differs therefrom only in the provision of an internal circumferential rib 33 in the equatorial plane of the ring. The location of such a rib in a ring-like structure with equal-width upper and lower walls 17 and 18 is best shown in FIG. 15, the location of such a rib in a ring-like structure with unequal-width upper and lower walls 17 and 18a is best shown in FIG. 15A, and the location of such a rib in a ring-like structure having unequal-width upper and lower walls with the lower wall 18a inclined posteriorly relative to the equatorial plane of the structure is best shown in FIG. 15B. It will be understood, of course, that the holes or depressions (indentations) 31 can optionally be omitted from the lower wall of the structure 16d or can be located on the upper wall thereof. It will further be understood that the presence of the rib 33 in the ring-like structure 16d effectively serves to define in the ring two separate compartments 34 and 35 which will be able to serve as respective receptacles for separate optical or mechanical devices to be inserted into the structure 16d. Merely by way of example, these devices may be a cylinder lens and a sphere lens to be used for astigmatism correction, with the cylinder lens being inserted in the anterior compartment 34 and the sphere lens being inserted in the posterior compartment 35; alternatively, the compartments may serve as separate receptacles for, e.g., the components of a compound lens system used for correcting for macular degeneration.

The same type of interior equatorial rib and the resultant dual compartment arrangement can be provided in a capsular bag-like structure such as is designated 20a in FIG. 16 and which differs from the ring-like structure 16d only in that the lower wall 22 is imperforate and extends across the entire expanse of the structure. The situation where the bottom wall 22 is substantially parallel to the equatorial plane of the structure is illustrated in FIG. 17, and the situation where the peripheral region 22a of the lower wall 22 is inclined posteriorly somewhat relative to the equatorial plane of the structure is illustrated in FIG. 17A.

As has been previously mentioned herein, the toroidal ring-like structures according to the present invention have an outer equatorial diameter which, on the one hand, is somewhat larger than the inner equatorial diameter of the patient's residual capsular bag if the ring is to be implanted in the residual capsular bag and, on the other hand, is correspondingly somewhat greater than the diameter of the ciliary sulcus if the ring is intended to be implanted into the region of the ciliary sulcus. In accordance with a further refinement of the present invention, it is proposed to facilitate the implantation of the both anteriorly and posteriorly incomplete capsular bag-derived ring-like structures by forming them so as to have a circumferentially compressible split washer-like configuration, with one of the end regions of the ring being tapered to a somewhat smaller transverse dimension than the interior groove of the structure at the other end region of the ring so that the smaller end region can be telescopically slidably received in the larger end region.

Representative versions of such circumferentially compressible ring-like structures are shown in FIGS. 18–24. Of these, the ring structure 16e (FIG. 18) is shown as having equal-width upper and lower walls 17 and 18, with the lower wall being provided at its inner periphery with a plurality of inwardly projecting tabs 36 in which respective holes or depressions (indentations) 31 are provided, and with the end region 37a of the ring being cross-sectionally tapered so as to fit telescopically slidably into the interior groove at the opposite end region 37b of the ring. As shown in FIG. 18, three tabs 36 are provided at 90° spacings from one another, with the tabs being located, for example, at the 3 o'clock, 9 o'clock and 12 o'clock positions (they could, of course, be located instead at the 3 o'clock, 6 o'clock and 9 o'clock positions or even otherwise) so as to locate the holes or depressions correspondingly. The structure 16f shown in FIG. 19, on the other hand, is similarly constructed but is provided with only two tabs 36 and respective holes or depressions 31; these have been illustrated as being located at, for example, the 6 o'clock and 12 o'clock positions, so that one of the tabs is located at the end region 37b of the ring while the other one is located at the other end of the same diameter of the ring-like structure, but by the same token the two tabs could be located at the 3 o'clock and 9 o'clock positions or even otherwise (not necessarily symmetrically). From FIGS. 18 and 19 it will be understood, therefore, that a ring-like structure of this type can be provided with four or more as well as with only two or three tabs 36 and holes or indentations 31. The ring-like structure 16g shown in FIG. 20 likewise duplicates the essence of the configuration of the ring 16e of FIG. 18 but differs therefrom in that in lieu of the three separate tabs 36 which characterize the structure 16e, the structure 16g is provided with one circumferentially extending tab or platform 38 projecting inwardly from the inner periphery of the lower wall 18 with the respective holes or depressions 31 being formed in the platform (the latter, of course, is discontinuous in the region of the interfitting ends 37a and 37b of the ring structure 16g).

The ring-like structure 16h shown in FIGS. 21 and 22 again has a circumferentially compressible split washer-like configuration characterized by telescopically interfitting opposite end regions 37a and 37b and equal-width upper and lower walls 17 and 18, but differs from the structures 16e, 16f and 16g in that the holes or depressions 31 are, as in the case of the ring-like structure 16a of FIG. 11, provided directly in the lower wall 18 rather than in tabs or platforms projecting therefrom. The configuration of the ring-like structure 16i shown in FIGS. 23 and 24 is essentially the same as that of the structure 16h except that the upper and lower walls 17 and 18a are of unequal widths, with the holes or depressions 31 being formed, as in the case of the ring-like structure 16c of FIG. 13, directly in the radially wider lower wall 18a rather than in tabs or platforms projecting therefrom.

By virtue of this construction, such a ring-like structure is circumferentially compressible from its nominal outer diameter to a diameter somewhat smaller than that of either the capsular bag or the ciliary sulcus into which it is to be implanted. Thus, when such a ring structure is so compressed, it will be easier for the surgeon to manipulate it into a position within the capsular bag or the ciliary sulcus, and then upon the compressive force being released, the structure will automatically expand back to or almost to its nominal diameter so as to be in firm circumferential engagement with the capsular bag or the ciliary sulcus. It should be understood, furthermore, that such circumferentially compressible ring-like structures as are shown in FIGS. 18–24 can also be provided with interior circumferentially extending radial ribs (similar to the ribs 33 shown in FIGS. 14–15B and 16–17A but differing therefrom in being circumferentially discontinuous in the regions of the split telescoping ends 37a–37b and here being illustrated by way of example only in FIGS. 21–24 and only in phantom outline) for dividing the internal grooves or channels of the ring-like structures into dual anterior and posterior compartments for the purposes previously described herein.

In accordance with yet another refinement of the present invention, it is contemplated that a circumferentially compressible ring-like structure may be provided which has a split washer-like configuration differing from that of the structures shown in FIGS. 18–24. As shown in FIG. 25, a ring-like structure 39 of this type may have the generally toroidal configuration of the various ring-like structures 16e to 16i herein disclosed, with equal width upper and lower walls 17 and 18 or with unequal width upper and lower walls (not shown in FIG. 25 but similar to the walls 17 and 18a of the embodiment of FIG. 23). The difference between the structures 16e–16i and the structure 39 is that the circumferential compressibility of the ring-like structure 39 is attained through the provision of a circumferential gap 40 between the opposite end regions 41a and 41b of the ring. Alternatively, as shown in FIG. 26, a split washer-like ring structure 42 utilizing the provision of a gap 43 between the opposite end regions 44a and 44b of the structure to achieve the desired circumferential compressibility may have a simple grooveless rod- or bar-shaped configuration with, for example, either a cross-sectionally square or rectangular form as shown in FIG. 27 or a cross-sectionally circular or oval form as shown in FIG. 27A. It will be understood that split rings of the types illustrated in FIGS. 25 and 26, either or both of which may be provided with holes or indentations 31, are capable of implantation either in the residual natural capsular bag or in the region of the ciliary sulcus. In the latter case, of course, the ring-like structures 39 and 42 would preferably be provided with outwardly directed sets of spines, which are not shown in FIGS. 25–27A but would have an appropriate one of the forms of the spines illustrated in FIGS. 28 and 29 at 27A, 27B and 27C, for enhancing the fixation of those structures to the sclera. Insofar as their use is concerned, the structures 39 and 42 can serve, when implanted into a residual natural capsular bag, as a means for expanding or stretching the capsular bag when that is needed, for example, in a case of pseudoexfoliation or in a case of physical trauma where the Zonules may be torn. A toroidal ring-like structure of the type shown in FIG. 25 can, of course, serve (whether implanted in the capsular bag or the ciliary sulcus) as a receptacle for an IOL or other device to be implanted in the patient's eye, and in such a case may also be provided with an interior circumferential rib (not shown in FIG. 25 but similar to those shown in FIGS. 21–24) defining dual anterior and posterior compartments in the groove of the ring, subject always to the requirement that the haptics or position fixation elements of such a device must be capable of being fully seated in the groove of the ring-like structure 39. On the other hand, a ciliary sulcus-mounted bar-shaped ring-like structure of the type shown in FIGS. 26–27A can serve as a platform for supporting a variety of implantable devices, such as artificial irises, intraocular lenses and compound lens systems, or other optical and/or mechanical devices.

It will be understood that the foregoing description of preferred embodiments of the present invention is for purposes of illustration only, and that the various structural and functional features herein disclosed are susceptible to a number of modifications and changes none of which entails any departure from the spirit and scope of the present invention as defined in the hereto appended claims.

I claim:

1. A "spare part" designed for use by a surgeon for surgical implantation into either the residual natural capsular bag or the ciliary sulcus of a patient's eye following an extracapsular or intracapsular cataract extraction, said "spare part" comprising a body made of a biocompatible sheet material preformed into the shape of an artificial either anteriorly incomplete and posteriorly complete or both anteriorly and posteriorly incomplete capsular bag-like structure, said artificial capsular bag-like structure having a peripheral generally toroidally ring-shaped equatorial region and including an annular anterior wall and an either annular or circular posterior wall connected to each other at their radially outwardmost peripheries and jointly defining between said walls a channel-shaped compartment for receiving an optical, mechanical or combined optical and mechanical device, and at least one of said anterior and posterior walls being provided on its respective anterior surface with a relatively compact series of degree markings which are distributed uniformly over at least one half of the circumference of said artificial capsular bag-like structure between two diametrically opposite locations on said anterior surface and at respective angular spacings of between about 3° and about 20° from each other and are visually perceptible by the surgeon within the patient's eye, after said artificial capsular bag-like structure has been inserted into the patient's eye, for facilitating achievement of a desired orientation of the axis of a cylinder lens component of an astigmatism-correcting intraocular lens when such intraocular lens is received in said compartment of said artificial capsular bag-like structure.

2. A "spare part" according to claim 1, wherein said artificial capsular bag-like structure is anteriorly incomplete and posteriorly complete, said anterior wall has the shape of an annular anterior capsular flap-like portion of said artificial capsular bag-like structure, and said posterior wall has the shape of an imperforate circular posterior capsule-like portion of said artificial capsular bag-like structure.

3. A "spare part" according to claim 1, wherein said artificial capsular bag-like structure is both anteriorly and posteriorly incomplete and thereby generally toroidally ring-shaped, and each of said anterior and posterior walls has the shape of an annular capsular flap-like portion of said toroidally ring-shaped artificial capsular bag-like structure.

4. A "spare part" according to claim 2 or 3, wherein said artificial capsular bag-like structure further comprises an interior rib located within said compartment and extending circumferentially along and projecting radially inwardly of said generally toroidally ring-shaped equatorial region of said artificial capsular bag-like structure, said rib constituting a partition dividing said compartment into two subcompartments adapted to serve as separate receptacles for respective optical or mechanical devices.

5. A "spare part" according to claim 2 or 3, wherein said artificial capsular bag-like structure further comprises a plurality of circumferentially spaced stiff but flexible spines located outside said compartment and projecting generally radially outwardly from the exterior surface of said generally toroidally ring-shaped equatorial region of said artificial capsular bag-like structure, said spines by virtue of their stiffness being adapted to penetrate into the sclera in the patient's eye in the region of the ciliary sulcus and the ciliary body for fixating said artificial capsular bag-like structure to the sclera.

6. A "spare part" according to claim 5, wherein said spines are arranged to perforate the entire thickness of the sclera and to project at respective locations beyond the outer surface of the sclera so as to provide each spine with a distal end region adapted to be bent into a hook-like portion capable of confinement between the outer surface of the sclera and an overlying section of Tenon's capsule.

7. A "spare part" according to claim 5, wherein said spines are arranged to perforate only a portion of the thickness of the sclera and to project at respective locations into a plurality of surgically opened incisions within the sclera so as to provide each spine with a distal end region adapted to be bent into a hook-like portion capable of confinement between the tissues of the sclera when the respective incision is closed.

8. A "spare part" according to claim 2 or 3, wherein a circumferential outer region of said posterior wall of said artificial capsular bag-like structure adjoining said generally toroidally ring-shaped equatorial region of said artificial capsular bag-like structure is inclined posteriorly relative to the equatorial plane of said artificial capsular bag-like structure, said posteriorly inclined outer region of said posterior wall serving, when said artificial capsular bag-like structure is implanted in the patient's residual natural capsular bag, to provide both an enhanced resistance to migration of epithelial cells over the natural posterior capsule and an enhanced resistance to posterior capsular opacification that tends to result in the patient's residual natural capsular bag from such epithelial cell migration.

9. A "spare part" according to claim 8, wherein the angle of inclination of said outer region of said posterior wall is in the range of about 10°–15°.

10. A "spare part" according to claim 8, wherein said artificial capsular bag-like structure further comprises an interior rib located within said compartment and extending circumferentially along and projecting radially inwardly of said generally toroidally ring-shaped equatorial region of said artificial capsular bag-like structure, said rib constituting a partition dividing said compartment into two subcompartments adapted to serve as separate receptacles for respective optical or mechanical devices.

11. A "spare part" according to claim 8, wherein said artificial capsular bag-like structure further comprises a plurality of circumferentially spaced stiff but flexible spines located outside said compartment and projecting generally radially outwardly from the exterior surface of said generally toroidally ring-shaped equatorial region of said artificial capsular bag-like structure, said spines by virtue of their stiffness being adapted to penetrate into the sclera in the patient's eye in the region of the ciliary sulcus and the ciliary body for fixating said artificial capsular bag-like structure to the sclera.

12. A "spare part" according to claim 11, wherein said artificial capsular bag-like structure further comprises an interior rib located within said compartment and extending circumferentially along and projecting radially inwardly of said generally toroidally ring-shaped equatorial region of said artificial capsular bag-like structure, said rib constituting a partition dividing said compartment into two subcompartments adapted to serve as separate receptacles for respective optical or mechanical devices.

13. A "spare part" according to claim 2 or 3, wherein said artificial capsular bag-like structure is further provided on at least one of said anterior and posterior walls thereof with a plurality of circumferentially spaced small holes or indentations which are visually perceptible by the surgeon within the patient's eye, after said artificial capsular bag-like structure has been inserted into the patient's eye, and are adapted to be engaged by a tool for facilitating manipulation of said artificial capsular bag-like structure.

14. A "spare part" according to claim 13, wherein said at least one of said anterior and posterior walls is provided with at least one tab or platform projecting from the inner peripheral edge of that wall radially inwardly of said toroidally ring-shaped artificial capsular bag-like structure, and said small holes or indentations are located on said at least one tab or platform.

15. A "spare part" according to claim 13, wherein said toroidally ring-shaped artificial capsular bag-like structure has a resilient split washer-like configuration with first and second separate end regions and a nominal outer equatorial diameter slightly larger than the inner equatorial diameter of the patient's natural capsular bag or the diameter of the patient's ciliary sulcus and is circumferentially resiliently compressible, whereby a circumferential compression of said toroidally ring-shaped artificial capsular bag-like structure facilitates insertion thereof into, and a subsequent relaxation of said circumferential compression of said toroidally ring-shaped artificial capsular bag-like structure permits a reexpansion thereof to exert an outwardly directed force on, the patient's natural capsular bag or ciliary sulcus.

16. A "spare part" according to claim 15, wherein said first end region of said toroidally ring-shaped artificial capsular bag-like structure is somewhat smaller in cross-sectional size than said second end region, and said first end region is telescopically slidably received in said second end region.

17. A "spare part" according to claim 15, wherein said first and second end regions of said toroidally ring-shaped artificial capsular bag-like structure are separated from one another by a circumferential gap therebetween, whereby said first and second end regions approach each other upon circumferential compression, and move away from each other upon relaxation of circumferential compression, of said toroidally ring-shaped artificial capsular bag-like structure.

18. A "spare part" according to claim 15, wherein said artificial capsular bag-like structure is further provided on at least one of said anterior and posterior walls thereof with a plurality of circumferentially spaced small holes or indentations which are visually perceptible by the surgeon within the patient's eye, after said artificial capsular bag-like structure has been inserted into the patient's eye, and are adapted to be engaged by a tool for facilitating manipulation shaped artificial capsular bag-like structure, and a series of degree markings located on one or the other of said anterior and posterior walls and distributed over at least one half of the circumference of said toroidally ring-shaped artificial capsular bag-like structure at respective angular spacings from each other of said toroidally ring-shaped artificial capsular bag-like structure.

19. A "spare part" according to claim 18, wherein said at least one of said anterior and posterior walls is provided with at least one tab or platform projecting from the inner peripheral edge of that wall radially inwardly of said toroidally ring-shaped artificial capsular bag-like structure, and said small holes or indentations are located on said at least one tab or platform.

20. A "spare part" according to claim 15, wherein said toroidally ring-shaped artificial capsular bag-like structure further comprises an interior rib located within said compartment and extending circumferentially along and projecting radially inwardly of the equatorial region of said toroidally ring-shaped artificial capsular bag-like structure, said rib constituting a partition dividing said compartment into two subcompartments adapted to serve as separate receptacles for respective optical or mechanical devices.

21. A "spare part" according to claim 15, wherein said toroidally ring-shaped artificial capsular bag-like structure further comprises a plurality of circumferentially spaced stiff but flexible spines located outside said compartment and projecting generally radially outwardly from the exterior surface of said equatorial region of said toroidally ring-shaped artificial capsular bag-like structure, said spines by virtue of their stiffness being adapted to penetrate into the sclera in the patient's eye in the region of the ciliary sulcus and the ciliary body for fixating said toroidally ring-shaped artificial capsular bag-like structure to the sclera.

22. A "spare part" according to claim 21, wherein said spines are arranged to perforate the entire thickness of the sclera and to project at respective locations beyond the outer surface of the sclera so as to provide each spine with a distal end region adapted to be bent into a hook-like portion capable of confinement between the outer surface of the sclera and an overlying section of Tenon's capsule.

23. A "spare part" according to claim 21, wherein said spines are arranged to perforate only a portion of the thickness of the sclera and to project at respective locations into a plurality of surgically opened incisions within the sclera so as to provide each spine with a distal end region adapted to be bent into a hook-like portion capable of confinement between the tissues of the sclera when the respective incision is closed.

24. A "spare part" designed for use by a surgeon for surgical implantation into either the residual natural capsular bag or the ciliary sulcus of a patient's eye following an extracapsular or intracapsular cataract extraction, said "spare part" comprising a body made of a biocompatible sheet material preformed into the shape of a generally ring-shaped structure, said ring-shaped structure having a circumferentially resiliently compressible split washer-like configuration with first and second separate end regions adapted for relative movement with respect to each other in the circumferential direction of said ring-shaped structure, and said ring-shaped structure, when intended for implantation into the residual natural capsular bag of the patient's eye, having a nominal outer diameter somewhat greater than the inner diameter of the residual natural capsular bag and, when intended for implantation into the ciliary sulcus of the patient's eye, having a nominal outer diameter somewhat greater than the diameter of the ciliary sulcus, wherein said first and second end regions of said ring-shaped structure are separated from one another by a circumferential gap therebetween, to permit said end regions to approach each other upon circumferential compression of said ring-shaped structure, and wherein said ring-shaped structure has a generally toroidal configuration with substantially annular anterior and posterior walls interrupted by said gap and extending from said first to said second end region and being connected to each other at their radially outwardmost peripheries, said anterior and posterior walls defining therebetween an equatorial, radially inwardly open, interior groove constituting a compartment in which an optical or mechanical or combined optical and mechanical device can be received, whereby upon circumferential compression of said ring-shaped structure by the surgeon, insertion thereof into the residual capsular bag or the ciliary sulcus, as the case may be, is facilitated, and upon release of such circumferential compression of said ring-shaped structure after insertion thereof, said ring-shaped structure exerts an outward force on the equatorial region of the residual natural capsular bag or on the ciliary sulcus, as the case may be.

25. A "spare part" according to claim 24 wherein said ring-shaped structure further comprises an interior rib located within said compartment and extending circumferentially along and projecting radially inwardly of said groove, said rib constituting a partition dividing said compartment into two subcompartments adapted to serve as separate receptacles for respective optical or mechanical devices.

26. A "spare part" according to claim 24, wherein said ring-shaped structure further comprises a plurality of circumferentially spaced flexible spines located outside said groove and projecting generally radially outwardly from the exterior peripheral surface of said ring-shaped structure, said spines being adapted to penetrate into the sclera in the patient's eye in the region of the ciliary sulcus and the ciliary body for fixating said ring-shaped structure to the sclera.

27. A "spare part" according to claim 26, wherein said ring-shaped structure further comprises an interior rib located within said compartment and extending circumferentially along and projecting radially inwardly of said groove, said rib constituting a partition dividing said compartment into two subcompartments adapted to serve as separate receptacles for respective optical or mechanical devices.

28. A "spare part" according to claim 26 or 27, wherein said spines are arranged to perforate the entire thickness of the sclera and to project at respective locations beyond the outer surface of the sclera so as to provide each spine with a distal end region adapted to be bent into a hook-like portion capable of confinement between the outer surface of the sclera and an overlying section of Tenon's capsule.

29. A "spare part" according to claim 26 or 27, wherein said spines are arranged to perforate only a portion of the thickness of the sclera and to project at respective locations into a plurality of surgically opened incisions within the sclera so as to provide each spine with a distal end region adapted to be bent into a hook-like portion capable of confinement between the tissues of the sclera when the respective incision is closed.

30. A "spare part" according to claim 24, 25 or 26, further comprising a plurality of circumferentially spaced visually perceptible small holes or indentations located on one or the other of said anterior and posterior walls of said ring-shaped structure and adapted to be engaged by a tool for facilitating manipulation of said ring-shaped structure.

31. A "spare part" according to claim 24, wherein said ring-shaped structure has a generally toroidal configuration with annular anterior and posterior walls extending from said first to said second end region and being connected to each other at their radially outwardmost peripheries, said anterior and posterior walls defining therebetween an equatorial, radially inwardly open, interior groove constituting a compartment in which an optical or mechanical or combined optical and mechanical device can be received, and said first end region of said ring-shaped structure is somewhat smaller in cross-sectional size than said second end region thereof, to permit said first end region to be telescopically slidably received in said second end region.

32. A "spare part" according to claim 31, wherein at least one of said anterior and posterior walls is provided with at least one tab or platform projecting from the inner peripheral edge of that wall radially inwardly of said ring-shaped structure, and at least one visually perceptible small hole or indentation is provided on each tab or platform and adapted to be engaged by a tool for facilitating manipulation of said ring-shaped structure.

33. A "spare part" according to claim 31, wherein said ring-shaped structure further comprises an interior rib located within said compartment and extending circumferentially along and projecting radially inwardly of said groove, said rib constituting a partition dividing said compartment into two subcompartments adapted to serve as separate receptacles for respective optical or mechanical devices.

34. A "spare part" according to claim 31, wherein said ring-shaped structure further comprises a plurality of circumferentially spaced flexible spines located outside said groove and projecting generally radially outwardly from the exterior peripheral surface of said ring-shaped structure, said spines being adapted to penetrate into the sclera in the patient's eye in the region of the ciliary sulcus and the ciliary body for fixating said ring-shaped structure to the sclera.

35. A "spare part" according to claim 34, wherein said ring-shaped structure further comprises an interior rib located within said compartment and extending circumferentially along and projecting radially inwardly of said groove, said rib constituting a partition dividing said compartment into two subcompartments adapted to serve as separate receptacles for respective optical or mechanical devices.

36. A "spare part" according to claim 34 or 35, wherein said spines are arranged to perforate the entire thickness of the sclera and to project at respective locations beyond the outer surface of the sclera so as to provide each spine with a distal end region adapted to be bent into a hook-like portion capable of confinement between the outer surface of the sclera and an overlying section of Tenon's capsule.

37. A "spare part" according to claim 34 or 35, wherein said spines are arranged to perforate only a portion of the thickness of the sclera and to project at respective locations into a plurality of surgically opened incisions within the sclera so as to provide each spine with a distal end region adapted to be bent into a hook-like portion capable of confinement between the tissues of the sclera when the respective incision is closed.

38. A "spare part" designed for use by a surgeon for surgical implantation into either the residual natural capsular bag or the ciliary sulcus of a patient's eye following an extracapsular or intracapsular cataract extraction, said "spare part" comprising a body made of a biocompatible sheet material preformed into the shape of an artificial either anteriorly incomplete and posteriorly complete or both anteriorly and posteriorly incomplete capsular bag-like structure, said artificial capsular bag-like structure having a peripheral generally toroidally ring-shaped equatorial region and including an annular anterior wall and an either annular or circular posterior wall connected to each other at their radially outwardmost peripheries and jointly defining between said walls a channel-shaped compartment for receiving an optical, mechanical or combined optical and mechanical device, and the wall formation of said artificial capsular bag-like structure in said equatorial region thereof where said anterior and posterior walls are connected to each other being devoid of any circumferential inwardly directed fold-like portion, and said artificial capsular bag-like structure further having an interior rib located within said compartment, said rib being secured to said wall portion and extending circumferentially along and projecting radially inwardly of said generally toroidally ring-shaped equatorial region of said artificial capsular bag-like structure from said wall formation and constituting a partition dividing said compartment into two subcompartments adapted to serve as separate receptacles for respective optical or mechanical devices.

39. A "spare part" according to claim 38, wherein said artificial capsular bag-like structure is anteriorly incomplete and posteriorly complete, said anterior wall has the shape of an annular anterior capsular flap-like portion of said artificial capsular bag-like structure, and said posterior wall has the shape of an imperforate circular posterior capsule-like portion of said artificial capsular bag-like structure.

40. A "spare part" according to claim 38, wherein said artificial capsular bag-like structure is both anteriorly and posteriorly incomplete and thereby generally toroidally ring-shaped, and each of said anterior and posterior walls has the shape of an annular capsular flap-like portion of said toroidally ring-shaped artificial capsular bag-like structure.

41. A "spare part" according to claim 39 or 40, wherein said artificial capsular bag-like structure is further provided on at least one of said anterior and posterior walls thereof with a plurality of circumferentially spaced small holes or indentations which are visually perceptible by the surgeon within the patient's eye, after said artificial capsular bag-like structure has been inserted into the patient's eye, and are adapted to be engaged by a tool for facilitating manipulation of said artificial capsular bag-like structure.

42. A "spare part" according to claim 41, wherein said at least one of said anterior and posterior walls is provided with at least one tab or platform projecting from the inner peripheral edge of that wall radially inwardly of said toroidally ring-shaped artificial capsular bag-like structure, and said small holes or indentations are located on said at least one tab or platform.

43. A "spare part" according to claim 39 or 40, wherein said artificial capsular bag-like structure further comprises a plurality of circumferentially spaced stiff but flexible spines located outside said compartment and projecting generally radially outwardly from the exterior surface of said generally toroidally ring-shaped equatorial region of said artificial capsular bag-like structure, said spines by virtue of their stiffness being adapted to penetrate into the sclera in the patient's eye in the region of the ciliary sulcus and the ciliary body for fixating said artificial capsular bag-like structure to the sclera.

44. A "spare part" according to claim 43, wherein said spines are arranged to perforate the entire thickness of the sclera and to project at respective locations beyond the outer surface of the sclera so as to provide each spine with a distal end region adapted to be bent into a hook-like portion capable of confinement between the outer surface of the sclera and an overlying section of Tenon's capsule.

45. A "spare part" according to claim 43, wherein said spines are arranged to perforate only a portion of the thickness of the sclera and to project at respective locations into a plurality of surgically opened incisions within the sclera so as to provide each spine with a distal end region adapted to be bent into a hook-like portion capable of confinement between the tissues of the sclera when the respective incision is closed.

46. A "spare part" according to claim 39 or 40, wherein a circumferential outer region of said posterior wall of said artificial capsular bag-like structure adjoining said generally toroidally ring-shaped equatorial region of said artificial capsular bag-like structure is inclined posteriorly relative to the equatorial plane of said artificial capsular bag-like structure, said posteriorly inclined outer region of said posterior wall serving, when said artificial capsular bag-like structure is implanted in the patient's residual natural capsular bag, to provide both an enhanced resistance to migration of epithelial cells over the natural posterior capsule and an enhanced resistance to posterior capsular opacification that tends to result in the patient's residual natural capsular bag from such epithelial cell migration.

47. A "spare part" designed for use by a surgeon for surgical implantation into either the residual natural capsular bag or the ciliary sulcus of a patient's eye following an extra-capsular or intracapsular cataract extraction, said "spare part" comprising a body made of a biocompatible sheet material preformed into the shape of an artificial either anteriorly incomplete and posteriorly complete or both anteriorly and posteriorly incomplete capsular bag-like structure, said artificial capsular bag-like structure having a peripheral generally toroidally ring-shaped equatorial region and including an annular anterior wall and an either annular or circular posterior wall connected to each other at their radially outwardmost peripheries and jointly defining between said walls a channel-shaped compartment for receiving an optical, mechanical or combined optical and mechanical device, and said artificial capsular bag-like structure further having a plurality of circumferentially spaced stiff but flexible spines located outside said compartment and projecting generally radially outwardly from the exterior of said toroidally ring-shaped equatorial region of said artificial capsular bag-like structure, said spines by virtue of their stiffness being adapted to penetrate into the sclera in the patient's eye in the region of the ciliary sulcus and the ciliary body for fixating said artificial capsular bag-like structure to the sclera.

48. A "spare part" according to claim 47, wherein said spines are arranged to perforate the entire thickness of the sclera and to project at respective locations beyond the outer surface of the sclera so as to provide each spine with a distal end region adapted to be bent into a hook-like portion capable of confinement between the outer surface of the sclera and an overlying section of Tenoh's capsule.

49. A "spare part" according to claim 47, wherein said spines are arranged to perforate only a portion of the thickness of the sclera and to project at respective locations into a plurality of surgically opened incisions within the sclera so as to provide each spine with a distal end region adapted to be bent into a hook-like portion capable of confinement between the tissues of the sclera when the respective incision is closed.

* * * * *

UNITED STATES PATENT AND TRADEMARK OFFICE
CERTIFICATE OF CORRECTION

PATENT NO.   : 5,628,795
DATED        : May 13, 1997
INVENTOR(S)  : David W. Langerman It is certified that error appears in the above-identified patent and that said Letters Patent is hereby corrected as shown below:

Claim 15, line 1, for "claim 13" read -- claim 3 --.
Claim 18, lines 8-14, for "to be engaged *** artificial capsular" read
         -- to be engaged by a tool for facilitating manipulation of said
         toroidally shaped artificial capsular --.
Claim 25, line 1, for "claim 24" read -- claim 24, --.
Claim 48, line 7, for "Tenoh's capsule" read -- Tenon's capsule --.

Signed and Sealed this

Twelfth Day of August, 1997

Attest:

BRUCE LEHMAN

Attesting Officer

Commissioner of Patents and Trademarks